United States Patent [19]

Cotrel et al.

[11] 4,407,797
[45] Oct. 4, 1983

[54] 1,2-DITHIOL-3-YLIDENEAMMONIUM DERIVATIVES, COMPOSITIONS AND USE

[75] Inventors: Claude Cotrel, Paris; Daniel Farge, Thiais; Gerard Taurand, Sucy-en-Brie, all of France

[73] Assignee: Rhone-Poulenc Sante, Courbevoie, France

[21] Appl. No.: 406,980

[22] Filed: Aug. 10, 1982

[30] Foreign Application Priority Data

Aug. 11, 1981 [FR] France .................................. 8115528
Jun. 17, 1982 [FR] France .................................. 8210616

[51] Int. Cl.$^3$ ................. A61K 31/535; A61K 31/385; C07D 339/04; C07D 413/04
[52] U.S. Cl. ............................. 424/246; 424/248.51; 424/250; 424/263; 424/267; 424/274; 424/277; 544/58.7; 544/85; 544/124; 544/131; 544/145; 544/357; 544/360; 544/379; 546/187; 546/193; 546/207; 546/281; 546/284; 548/527; 546/214
[58] Field of Search ............... 544/58.7, 85, 124, 131, 544/145, 357, 360, 379; 546/187, 193, 207, 214, 281, 284; 548/527; 549/36, 37; 260/330.3; 424/246, 248.51, 250, 263, 267, 274, 277

[56] References Cited

U.S. PATENT DOCUMENTS 3,676,459  7/1972  Bader et al. ........................... 549/36

Primary Examiner—Robert W. Ramsuer
Attorney, Agent, or Firm—Stevens, Davis, Miller & Mosher

[57] ABSTRACT

New compounds of the formula:

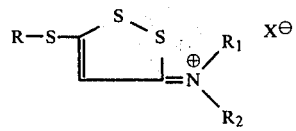

wherein $X^{\ominus}$ is an anion, R is ($C_{1-7}$) alkyl [unsubstituted or substituted by hydroxy, carboxy, alkoxycarbonyl, cyano, dialkylamino, alkylcarbonyl, or benzoyl which is unsubstituted or substituted by one or more halogen atoms or radicals selected from alkyl (optionally substituted by one or more halogens), alkoxy, hydroxy, amino, alkylamino, dialkylamino, cyano and nitro, or by a thenoyl radical (which is unsubstituted or substituted by one or more halogens or radicals selected from alkyl, cyano and nitro), or a pyridinecarbonyl, carbamoyl or dialkylcarbamoyl radical (the alkyl radicals of which can form a 5-membered or 6-membered heterocyclic ring) or a pyridyl radical], dialkylcarbamoyl (the alkyl radicals of which can form a 5-membered or 6-membered heterocyclic ring), ($C_{2-4}$) alkenyl, ($C_{2-4}$) alkynyl, alkoxycarbonyl or a 2-oxotetrahydrofuran-3-yl or 2-oxotetrahydropyran-3-yl ring, and either $R_1$ and $R_2$ are phenyl, cycloalkyl, alkyl or phenylalkyl or together form a 5-membered to 7-membered heterocyclic ring, or $R_1$ is phenyl optionally substituted by one or more halogen atoms or radicals selected from alkyl optionally substituted by one or more halogens, alkoxy, hydroxy, amino, alkylamino, dialkylamino, cyano and nitro, or alternatively is cycloalkyl, alkyl or phenylalkyl, and $R_2$ is a hydrogen atom, are useful as cytoprotective anti-ulcer agents.

16 Claims, No Drawings

1,2-DITHIOL-3-YLIDENEAMMONIUM DERIVATIVES, COMPOSITIONS AND USE

DESCRIPTION

The present invention relates to new therapeutically useful 1,2-dithiol-3-ylideneammonium derivatives, to processes for their preparation and pharmaceutical compositions containing them.

The 1,2-dithiol-3-ylideneammonium derivatives of the present invention are those compounds of the general formula:

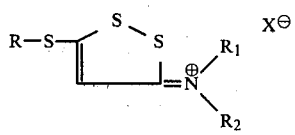 (I)

wherein $X^\ominus$ represents an anion, R represents a straight- or branched-chain alkyl radical containing 1 to 7 carbon atoms [unsubstituted or substituted by a hydroxy, carboxy, alkoxycarbonyl, cyano, dialkylamino or alkylcarbonyl radical or a benzoyl radical the phenyl ring of which is unsubstituted or substituted by one or more halogen atoms or radicals selected from alkyl (optionally substituted by one or more halogen atoms), alkoxy, hydroxy, amino, alkylamino, dialkylamino, cyano and nitro, or a thenoyl radical the thienyl ring of which is unsubstituted or substituted by one or more halogen atoms or radicals selected from alkyl, cyano and nitro, or a pyridylcarbonyl, carbamoyl, dialkylcarbamoyl (the alkyl radicals of which can together form, with the nitrogen atom to which they are attached, a 5- or 6-membered heterocyclic ring optionally containing another hetero-atom selected from oxygen, sulphur, and nitrogen substituted by an alkyl or alkylcarbonyl radical) or pyridyl radical], a dialkylcarbamoyl radical (the alkyl radicals of which can together form, with the nitrogen atom to which they are attached, a 5- or 6-membered heterocyclic ring optionally containing another hetero-atom selected from oxygen, sulphur, and nitrogen substituted by an alkyl or alkylcarbonyl radical), an alkenyl radical containing 2 to 4 carbon atoms, an alkynyl radical containing 2 to 4 carbon atoms, or an alkoxycarbonyl radical, or alternatively represents a 2-oxotetrahydrofuran-3-yl or 2-oxotetrahydropyran-3-yl ring, and either $R_1$ and $R_2$, which have the same or different significances, each represent a phenyl radical, a cycloalkyl radical containing 3 to 7 carbon atoms, or an alkyl or phenylalkyl radical, or alternatively together form, with the nitrogen atom to which they are attached, a 5-, 6- or 7-membered heterocyclic ring which can optionally contain another hetero-atom selected from oxygen, sulphur, and nitrogen substituted by an alkyl radical (e.g. pyrrolidin-1-yl, piperidino, morpholino and perhydroazepin-1-yl), or $R_1$ represents a phenyl radical unsubstituted or substituted by one or more halogen atoms or radicals selected from alkyl (optionally substituted by one or more halogen atoms), alkoxy, hydroxy, amino, alkylamino, dialkylamino, cyano and nitro, or alternatively represents a cycloalkyl radical containing 3 to 7 carbon atoms, or an alkyl or phenylalkyl radical, and $R_2$ represents a hydrogen atom, and also the corresponding bases (viz. no anion $X^\ominus$ is present) when $R_2$ represents hydrogen. It is to be understood that, unless otherwise mentioned, the alkyl and alkoxy radicals and moieties which have been heretofore mentioned or are mentioned hereafter contain 1 to 4 carbon atoms in a straight- or branched-chain.

According to a feature of the present invention, the compounds of general formula (I) are prepared by reacting a compound of the general formula:

$$R\text{-}X_1 \qquad \text{(II)}$$

(wherein R is as hereinbefore defined and $X_1$ represents a halogen atom such as chlorine, bromine or iodine, or another reactive ester radical such as a mesyloxy or tosyloxy radical) with a 1,2-dithiol-3-thione of the general formula:

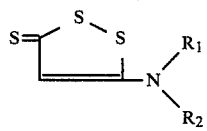 (III)

wherein $R_1$ and $R_2$ are as hereinbefore defined, and then isolating the product of general formaula (I) obtained and, optionally, converting it to another salt or to the corresponding base when $R_2$ represents a hydrogen atom.

The reaction can be carried out in an inert organic solvent at a temperature between 40° C. and the reflux temperature of the reaction mixture.

In order to increase the reactivity of the compound $R\text{-}X_1$ in the case when $X_1$ is different from an iodine atom, it is frequently advantageous to add at least a stoichiometric amount of sodium iodide to the reaction mixture; the salt isolated in this case is generally the iodide.

When appropriate, an acid addition salt of the reactant of general formula (II) may be used.

The 1,2-dithiol-3-thiones of general formula (III) can be prepared by cycling a propionic acid ester of the general formula:

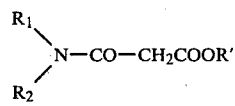 (IV)

wherein $R_1$ and $R_2$ are as hereinbefore defined and $R'$ represents an alkyl radical, by means of a thionating reagent, such as $P_4S_{10}$ or PEDERSEN-LAWESSON's reagent [i.e. 2,4-bis(4-methoxyphenyl)-2,4-dithioxo-1,3-dithia-2,4-diphosphetane]. The reaction is carried out under conditions analogous to those described by B. S. PEDERSEN and S. O. LAWESSON, Tetrahedron 35, 2433 (1979).

The propionic acid esters of general formula (IV) can be prepared by reacting an amine of the general formula:

 (V)

(wherein $R_1$ and $R_2$ are as hereinbefore defined) with an alkyl chloroformylacetate, or in accordance with the method of F. D. CHATTAWAY et al., J. Chem. Soc. 97, 939 (1910).

The new compounds of general formula (I) wherein R₂ represents a hydrogen atom obtained by the afore-described process can be converted to the corresponding bases by reaction with an alkali metal bicarbonate, sodium hydroxide or potassium hydroxide, in an aqueous medium. If the base precipitates in the medium, it is isolated by filtration; otherwise, it is extracted with the aid of an organic solvent. The base can be obtained directly, without isolating the intermediate salt, by carrying out the condensation of the compounds of general formulae (II) and (III) in the presence of a proton acceptor, such as triethylamine.

The bases thus derived from compounds of general formula (I) can be converted to acid addition salts by the addition of acids, in suitable solvents. Examples of suitable solvents are alcohols, ketones, ethers or chlorinated hydrocarbons. The acid addition salt formed precipitates, if necessary after concentration or its solution; the salt is separated by filtration or decantation.

According to another feature of the present invention, the new compounds of general formula (I) wherein $R_1$ represents a phenyl, cycloalkyl, alkyl or phenylalkyl radical and $R_2$ represents a cycloalkyl, alkyl or phenylalkyl radical, are also prepared by reacting a compound of the general formula:

$$R'_2 X_2 \qquad (VI)$$

wherein $R'_2$ represents a cycloalkyl, alkyl or phenylalkyl radical and $X_2$ represents a haloen atom or another reactive ester radical, such as mesyloxy or tosyloxy radical, with a product of general formula (I) wherein $R_1$ represents a phenyl, cycloalkyl, alkyl or phenylalkyl radicals and $R_2$ represents a hydrogen atom.

The reaction can be carried out in an inert organic solvent normally used when quaternising an amine.

The products of the general formula (I) can be converted to another salt by any trans-salification method known per se and which is compatible with the nature of the initial anion.

The compounds of general formula (I) can be purified by the usual methods, in particular by crystallisation or chromatography.

1,3-Dithiol-3-ylideneamine derivatives are known from the publication of F. BOBERG et al., J. Prakt. Chem. 315, 970 (1973), from the publication of G. CAILLAUD and Y. MOLLIER, Bull. Soc. Chim. France 72, 147 (1972), and from French Pat. No. 2011918. The products described in the said patent are presented as agricultural antifungal agents. None of the three publications mentioned above indicates pharmacological properties for the products described.

The new 1,2-dithiol-3-ylideneammonium derivatives of general formula (I) and their bases, when they exist, possess valuable pharmacological properties which render them useful as cytoprotective anti-ulcer agents.

They are active in particular in the ethanol ulcer test at doses of between 1 and 100 mg/kg animal body weight, administered orally to rats in accordance with the technique of A. ROBERT, Gastroenterology, 77, 433 (1979).

Compounds of general formula (I) of particular interest are those wherein R represents an alkyl radical containing 2 to 4 carbon atoms, or a straight- or branched-chain alkyl radical containing 1 to 7 carbon atoms [unsubstituted or substituted by a cyano, dialkylamino, carbamoyl, alkylcarbonyl or thenoyl radical, or a benzoyl radical the phenyl ring of which is unsubstituted or substituted by one or more halogen atoms or radicals selected from alkyl, alkoxy, hydroxy and cyano] and $R_1$ and $R_2$ together with the nitrogen atom to which they are attached represent a pyrrolidin-1-yl or morpholino radical.

Compounds of more outstanding interest are those compounds of general formula I wherein R represents a methyl or ethyl radical unsubstituted or substituted by a benzoyl radical the phenyl ring of which is unsubstituted or substituted by one or more halogen atoms or radicals selected from alkyl, alkoxy, hydroxy and cyano, and $R_1$ and $R_2$ together with the nitrogen atom to which they are attached represent the morpholino radical.

Of very special interest are the following compounds:
N-[5-(4-chlorophenacylthio)-1,2-dithiol-3-ylidene]-morpholinium chloride,
N-[5-(3-methoxyphenacylthio)-1,2-dithiol-3-ylidene]-morpholinium chloride,
N-[5-(4-fluorophenacylthio)-1,2-dithiol-3-ylidene]-morpholinium chloride,
N-[5-(2,4-dichlorophenacylthio)-1,2-dithiol-3-ylidene]-morpholinium chloride,
N-[5-(2-chlorophenacylthio)-1,2-dithiol-3-ylidene]-morpholinium iodide,
N-[5-(4-hydroxyphenacylthio)-1,2-dithiol-3-ylidene]-morpholinium chloride,
N-[5-(4-methoxyphenacylthio)-1,2-dithiol-3-ylidene]-morpholinium iodide,
N-[5-(4-methylphenacylthio)-1,2-dithiol-3-ylidene]-morpholinium chloride,
N-[5-(4-cyanophenacylthio)-1,2-dithiol-3-ylidene]-morpholinium chloride and
N-[5-(phenacylthio)-1,2-dithiol-3-ylidene]-morpholinium chloride.

The medicinal purposes, the compounds of general formula (I) are used in the form of bases, when they exist, or in the form of pharmaceutically acceptable salts obtained either directly by condensation of the compounds of the general formulae (II) and (III), or (I) and (VI), or by salification of the free bases, when they exist, or alternatively by trans-salification, as stated above.

As anions which can lead to pharmaceutically acceptable salts, there may be mentioned inorganic anions (such as chlorides, bromides, iodides, sulphates, nitrates and phosphates) or organic anions (such as acetates, propionates, succinates, benzoates, fumarates, maleates, theophylline-acetates, salicylates, phenolphthalinates and methylene-bis-β-hydroxynaphthoates).

The following non-limitative Examples illustrate the preparation of compounds of the present invention.

EXAMPLE 1

Methyl iodide (21.3 g) is added to a suspension of 5-dimethylamino-1,2-dithiol-3-thione (17.7 g) in acetone (350 cc) and the mixture is heated under reflux for 1 hour. After cooling, the insoluble product formed is filtered off and washed with acetone (2×20 cc). After two successive recrystallisations of the crude product from water, N-(5-methylthio-1,2-dithiol-3-ylidene)-dimethylammonium iodide (14.2 g), melting at 226° C., is obtained.

5-Dimethylamino-1,2-dithiol-3-thione can be prepared by reacting ethyl 3-dimethylamino-3-oxopropionate (51 g) with phosphorus pentasulphide (107.5 g) in pyridine (640 cc) under reflux for 1 hour. After cooling to a temperature of about 20° C., the reaction mixture is poured into water (6.4 liters) and the insoluble product is extracted with methylene chloride (1 liter). The aqueous phase is then separated by decantation and washed with methylene chloride (2×500 cc). The methylene chloride phases are combined, dried over sodium sulphate and then concentrated to dryness under reduced pressure (20 mm Hg; 2.7 kPa) at 40° C. The residue is dissolved in methylene chloride (1 liter) and the solution thus obtained is poured onto silica gel (1.1 kg) contained in a column of diameter 5.9 cm. Elution is carried out with methylene chloride (8 liters); this eluate is discarded. Elution is then carried out with methylene chloride (4 liters) and the corresponding eluate is concentrated to dryness under reduced pressure (20 mm Hg; 2.7 kPa) at 40° C. The residue obtained is taken up in ethyl acetate (20 cc) and the insoluble product is filtered off and washed with ethyl acetate (2×10 cc). After drying, 5-dimethylamino-1,2-dithiol-3-thione (8.6 g), melting at 193° C., is obtained.

Ethyl 3-dimethylamino-3-oxopropionate can be prepared in accordance with the method described by A. Ermili et al., J. Org. Chem. 30, 339 (1965).

EXAMPLE 2

A solution of methyl iodide (1.42 g) in acetone (4 cc) is added to a solution of 5-diethylamino-1,2-dithiol-3-thione (1.45 g) in acetone (25 cc) under reflux, and the reaction mixture is kept under reflux for 1 hour 30 minutes. After cooling to a temperature of about 20° C., the insoluble product formed is filtered off and washed with acetone (3×5 cc) and then with diisopropyl ether (2×5 cc). By recrystallisation of the resulting product from ethanol (8.7 cc), N-(5-methylthio-1,2-dithiol-3-ylidene)-diethylammonium iodide (2 g), melting at 159° C., is obtained.

5-Diethylamino-1,2-dithiol-3-thione can be prepared by reacting phosphorus pentasulphide (12.4 g) with ethyl 3-diethylamino-3-oxopropionate (7 g) in pyridine (92 cc) under reflux for 1 hour. The reaction mixtue is cooled to a temperature of about 20° C., treated with water (925 cc) and extracted with methylene chloride (successively 105 cc and 2×75 cc). The organic phases are combined, washed with 4 N ammonium solution (3×50 cc) and then with distilled water (50 cc), dried over magnesium sulphate and filtered, and the filtrate is concentrated to dryness under reduced pressure (20 mm Hg; 2.7 kPa) at 40° C. The residue obtained is dissolved in methylene chloride (10 cc) and the solution obtained is poured onto silica gel (110 g) contained in a column of diameter 3 cm. Elution is carried out first with methylene chloride (650 cc); the corresponding eluate is discarded. Elution is then carried out with methylene chloride (1,500 cc); the corresponding eluate is concentrated to dryness under reduced pressure (20 mm Hg; 2.7 kPa) at 40° C. The residue obtained is taken up in diethyl ether (5 cc) and the insoluble product is filtered off and then washed with diethyl ether (3×3 cc). After drying, 5-diethylamino-1,2-dithiol-3-thione (1.5 g), melting at 93° C., is obtained.

Ethyl 3-diethylamino-3-oxopropionate can be prepared by reacting diethylamine (7.3 g) with ethyl chloroformylacetate (15 g), in the presence of triethylamine (10.1 g), in methylene chloride (100 cc) at a temperature of about 20° C. for 2 hours. After hydrolysis with distilled water (100 cc), the organic phase is washed successively with a 1 N aqueous solution of hydrochloric acid (100 cc), distilled water (4×35 cc), a 0.4% aqueous solution of sodium bicarbonate (178 cc) and finally distilled water (75 cc), and is then dried over magnesium sulphate and filtered, and the filtrate is concentrated to dryness under reduced pressure (20 mm Hg; 2.7 kPa) at 40° C. This gives ethyl 3-diethylamino-3-oxopropionate (14.6 g) in the form of an orange oil. [Rf=0.64; chromatography on a thin layer of silica gel, solvent: ethyl acetate].

EXAMPLE 3

A solution of methyl iodide (2.35 g) in acetone (7 cc) is added to a solution of 5-(N-methylbutylamino)-1,2-dithiol-3-thione (2.5 g) in acetone (38 cc) under reflux, and reflux is maintained for 1 hour 30 minutes. After cooling to a temperature of about 20° C., the insoluble product formed is filtered off and washed with acetone (3×5 cc) and then with diethyl ether (2×5 cc).

By recrystallisation of the resulting product from ethanol (19 cc), N-methyl-N-(5-methylthio-1,2-dithiol-3-ylidene)-butylammonium iodide (2.95 g), melting at 135° C., is obtained.

5-(N-Methylbutylamino)-1,2-dithiol-3-thione can be prepared by reacting phosphorous pentasulphide (114 g) with ethyl 3-(N-methylbutylamino)-3-oxopropionate (69.4 g) in pyridine (850 cc) under reflux for 1 hour. The reaction mixture is then cooled to a temperature of about 20° C. and then hydrolysed with distilled water (8.5 liters) and extracted with methylene chloride (980 cc and then 2×700 cc). The organic phases are combined, washed with 4 N ammonia solution (3×460 cc) and then with distilled water (460 cc), dried over magnesium sulphate, in the presence of decolorising charcoal, and filtered, and the filtrate is concentrated to dryness under reduced pressure (20 mm Hg; 2.7 kPa) at 40° C. The residue is dissolved in methylene chloride (100 cc) and the solution obtained is poured onto silica gel (1000 g) contained in a column of diameter 6 cm. Elution is carried out first with methylene chloride (2300 cc); the corresponding eluate is discarded. Elution is then carried out with methylene chloride (13.6 liters); the corresponding eluate is concentrated to dryness under reduced pressure (20 mm Hg; 2.7 kPa) at 40° C. The residue thus obtained is dissolved in methylene chloride (50 cc) and the solution is poured onto silica gel (400 g) contained in a column of diameter 4 cm. Elution is carried out with methylene chloride (750 cc); the corresponding eluate is discarded. Elution is then carried out with methylene chloride (1600 cc); the corresponding eluate is concentrated to dryness under reduced pressure (20 mm Hg; 2.7 kPa) at 40° C. This gives 5-(N-methylbutylamino)-1,2-dithiol-3-thione (12.7 g) in the form of an orange oil.

[Rf=0.78; chromatography on a thin layer of silica gel; solvent: ethyl acetate].

Ethyl 3-(N-methylbutylamino)-3-oxopropionate can be prepared by reacting N-methylbutylamine (34.7 g) with ethyl chloroformylacetate (60 g), in the presence of triethylamine (40.3 g), in methylene chloride (400 cc) at a temperature of about 20° C. for 2 hours. After hydrolysis with distilled water (400 cc), the organic phase is washed successively with a 1 N aqueous solution of hydrochloric acid (325 cc), distilled water (300 cc and then 2×145 cc), a 0.44% aqueous solution of sodium bicarbonate (310 cc) and distilled water (300 cc), dried over magnesium sulphate and filtered, and the filtrate is concentrated to dryness under reduced pressure (20 mm Hg; 2.7 kPa) at 40° C. This gives ethyl 3-(N-methylbutylamino)-3-oxopropionate (69.4 g) in the form of an orange oil.

[Rf=0.52; chromatography on a thin layer of silica gel; solvent: ethyl acetate].

EXAMPLE 4

A solution of methyl iodide (5.55 g) in acetone (10 cc) is added to a solution of 5-(N-methylphenethylamino)-1,2-dithiol-3-thione (3.5 g) in acetone (45 cc) under reflux, and the reaction mixture is kept under reflux for 1 hour 30 minutes. After cooling to a temperature of about 20° C., the insoluble product formed is filtered off and washed with acetone (10 cc).

By recrystallisation of the resulting product from ethanol (600 cc), N-methyl-N-(5-methylthio-1,2-dithiol-3-ylidene)-phenethylammonium iodide (4.6 g), melting at 186°–187° C., is obtained.

5-(N-Methylphenethylamino)-1,2-dithiol-3-thione can be prepared by reacting phosphorus pentasulphide (38.4 g) with ethyl 3-(N-methylphenethylamino)-3-oxopropionate (28.7 g) in pyridine (290 cc) under reflux for 1 hour. The reaction mixture is then cooled to a temperature of about 20° C. and hydrolysed with distilled water (3,500 cc) and extracted with methylene chloride (6×500 cc). The organic phases are combined, washed with distilled water (4×400 cc), dried over magnesium sulphate and concentrated to dryness under reduced pressure (20 mm Hg; 2.7 kPa) at 40° C. The residue is dissolved in methylene chloride (100 cc) and the solution is poured onto silica gel (1,200 g) contained in a column of diameter 6 cm. Elution is carried out first with methylene chloride (3,700 cc); the corresponding eluate is discarded. Elution is then carried out with methylene chloride (5,700 cc); the corresponding eluate is concentrated to dryness under reduced pressure (20 mm Hg; 2.7 kPa) at 40° C. The residue is recrystallised from ethyl acetate (25 cc). This gives 5-(N-methylphenethylamino)-1,2-dithiol-3-thione (3.7 g) melting at 96°–98° C.

Ethyl 3-(N-methylphenethylamino)-3-oxopropionate can be prepared by reacting N-methylphenethylamine (15.6 g) with ethyl chloroformylacetate (18.7 g) in the presence of triethylamine (12.6 g), in methylene chloride (125 cc) at a temperature of about 20° C. for 3 hours. After hydrolysis with distilled water (100 cc), the organic phase is washed with a 1 N aqueous solution of hydrochloric acid (100 cc) and when with distilled water (2×100 cc), dried over magnesium sulphate and filtered, and the diltrate is concentrated to dryness under reduced pressure (20 mm Hg; 2.7 kPa) at 40° C. This gives ethyl 3-(N-methylphenethylamino)-3-oxopropionate (28.7 g) in the form of an orange oil.

[Rf=0.64; chromatography on a thin layer of silica gel; solvent: ethyl acetate].

EXAMPLE 5

A solution of methyl iodide (6.3 g) in acetone (10 cc) is added to a solution of 5-(N-methylbenzylamino)-1,2-dithiol-3-thione (3.6 g) in acetone (45 cc) under reflux, and reflux is maintained for 1 hour. After cooling to a temperature of about 20° C., the insoluble product formed is filtered off and washed with acetone (15 cc).

By recrystallisation of the resulting product from ethanol (200 cc), N-methyl-N-(5-methylthio-1,2-dithiol-3-ylidene)-benzylammonium iodide (3.7 g), melting at 171°–173° C., is obtained.

5-(N-Methylbenzylamino)-1,2-dithiol-3 -thione can be prepared by reacting phosphorus pentasulphide (93 g) with ethyl 3-(N-methylbenzylamino)-3-oxopropionate (66 g) in pyridine (650 cc) under reflux for 1 hour. After cooling to a temperature of about 20° C., the reaction mixture is hydrolysed with distilled water (6 liters) and extracted with methylene chloride (5×500 cc). The organic phases are combined, washed successively with distilled water (2×500 cc), 2 N ammonia solution (1000 cc) and distilled water (2×500 cc), dried over magnesium sulphate and filtered, and the filtrate is concentrated to dryness under reduced pressure (20 mm Hg; 2.7 kPa) at 40° C. The residue is dissolved in methylene chloride (100 cc) and the solution is poured onto silica gel (1000 g) contained in a column of diameter 5.5 cm. Elution is carried out first with methylene chloride (6 liters); the corresponding eluate is discarded. Elution is then carried out with methylene chloride (10 liters); the corresponding eluate is concentrated to dryness under reduced pressure (20 mm Hg; 2.7 kPa) at 40° C. The residue is taken up in ethyl acetate (85 cc) and the insoluble product is filtered off. After drying, 5-(N-methylbenzylamino)-1,2-dithiol-3-thione (13.3 g), melting at 138°–140° C., is obtained.

Ethyl 3-(N-methylbenzylamino)-3-oxopropionate can be prepared by reacting N-methylbenzylamine (36.3 g) with ethyl chloroformylacetate (45.2 g), in the presence of triethylamine (30.3 g), in methylene chloride (300 cc) at 20° C. for 4 hours. After hydrolysis of the reaction mixture with distilled water (300 cc), the organic phase is washed with distilled water (300 cc) and then with a 1 N aqueous solution of hydrochloric acid (300 cc) and distilled water (2×300 cc). It is then dried over magnesium sulphate and filtered, and the filtrate is concentrated to dryness under reduced pressure (20 mm Hg; 2.7 kPa) at 40° C. This gives ethyl 3-(N-methylbenzylamino)-3-oxopropionate (66 g) in the form of a pale yellow oil.

[Rf=0.65; chromatography on a thin layer of silica gel; solvent: ethyl acetate].

EXAMPLE 6

A solution of methyl iodide (2.66 g) in acetone (8 cc) is added to a solution of 5-(N-methylphenylamino)-1,2-dithiol-3-thione (3 g) in acetone (43 cc) under reflux, and the reaction mixture is kept under reflux for 1 hour. After cooling to a temperature of about 20° C., the insoluble product formed is filtered off and washed with acetone (3×10 cc) and then with diisopropyl ether (3×10 cc).

By recrystallisation of the resulting product from a mixture of ethanol (50 cc) and distilled water (50 cc), N-methyl-N-(5-methylthio-1,2-dithiol-3-ylidene)-phenylammonium iodide (4.3 g), melting at 204° C. with decomposition, is obtained.

5-(N-Methylphenylamino)-1,2-dithiol-3-thione can be prepared by reacting phosphorus pentasulphide (127 g) with ethyl 3-(N-methylphenylamino)-3-oxopropionate (85 g) in pyridine (950 cc) under reflux for 1 hour. After cooling to a temperature of about 20° C., the reaction mixture is hydrolysed with distilled water (7 liters) and extracted with methylene chloride (3×900 cc). The organic phases are combined and washed with 4 N ammonia solution (3×500 cc) and then with distilled water (500 cc), dried over magnesium sulphate and filtered, and the filtrate is concentrated to dryness under reduced pressure (20 mm Hg; 2.7 kPa) at 40° C. The residue obtained is dissolved in methylene chloride (100 cc) and the solution is poured onto silica gel (1,000 g) contained in a column of diameter 6.5 cm. Elution is carried out first with methylene chloride (1,000 cc); the corresponding eluate is discarded. Elution is then carried out with methylene chloride (16.5 liters); the corresponding eluate is concentrated to dryness under reduced pressure (20 mm Hg; 2.7 kPa) at 40° C. The residue is taken up in ethyl acetate (20 cc) and the insoluble product is filtered off and washed with ethyl acetate (4×5 cc). This gives 5-(N-methylphenylamino)-1,2-dithiol-3-thione (10.7 g), melting at 128° C.

Ethyl 3-(N-methylphenylamino)-3-oxopropionate can be prepared by reacting N-methylphenylamine (42.6 g) with ethyl chloroformylacetate (60 g), in the presence of triethylamine (40.3 g), in methylene chloride (400 cc) at a temperature of about 20° C. for 2 hours. After hydrolysis with distilled water (400 cc), the organic phase is washed successively with a 1 N aqueous solution of hydrochloric acid (250 cc), distilled water (4×150 cc), a 0.45% aqueous solution of sodium bicarbonate (310 cc) and distilled water (300 cc), dried over magnesium sulphate and filtered, and the filtrate is concentrated to dryness under reduced pressure (20 mm Hg; 2.7 kPa) at 40° C. This gives ethyl 3-(N-methylphenylamino)-3-oxopropionate (85 g) in the form of an orange oil.

[Rf=0.63; chromatography on a thin layer of silica gel; solvent: ethyl acetate].

The product can be distilled at 138°-142° C. under 0.5 mm Hg (0.067 kPa).

EXAMPLE 7

A solution of methyl iodide (3.45 g) in acetone (11 cc) is added to a solution of 5-(N-methylcyclohexylamino)-1,2-dithiol-3-thione (4 g) in acetone (55 cc) under reflux, and reflux is maintained for 1 hour. After cooling to a temperature of about 20° C., the insoluble product formed is filtered off and then washed with acetone (3×20 cc) and diethyl ether (2×20 cc).

By recrystallisation of the resulting product from a mixture of ethanol (50 cc) and distilled water (50 cc), N-methyl-N-(5-methylthio-1,2-dithiol-3-ylidene)-cyclohexylammonium iodide (5 g), melting at 206° C., is obtained.

5-(N-Methylcyclohexylamino)-1,2-dithiol-3-thione can be prepared by reacting phosphorus pentasulphide (149 g) with ethyl 3-(N-methylcyclohexylamino)-3-oxopropionate (97 g) in pyridine (1110 cc) under reflux for 1 hour. After cooling to a temperature of about 20° C., the reaction mixture is hydrolysed with distilled water (6.5 liters) and then extracted with methylene chloride (1,300 cc and then 2×950 cc). The organic phases are combined, washed with distilled water (3×600 cc), dried over magnesium sulphate, in the presence of decolorising charcoal, and filtered, and the filtrate is concentrated to dryness under reduced pressure (20 mm Hg; 2.7 kPa) at 40° C. The residue is dissolved in methylene chloride (100 cc) and the solution is poured onto silica gel (1,500 cc) contained in a column of diameter 9 cm. Elution is carried out first with methylene chloride (2.6 liters); the corresponding eluate is discarded. Elution is then carried out with methylene chloride (8.5 liters); the corresponding eluate is concentrated to dryness under reduced pressure (20 mm Hg; 2.7 kPa) at 40° C. The residue is taken up in ethyl acetate (100 cc) and the insoluble product is filtered off and washed with ethyl acetate (4×20 cc) and then with diethyl ether (2×20 cc). After drying, 5-(N-methylcyclohexylamino)-1,2-dithiol-3-thione (20 g), melting at 107° C., is obtained.

Ethyl 3-(N-methylcyclohexylamino)-3-oxopropionate can be prepared by reacting N-methylcyclohexylamine (52.6 g) with ethyl chloroformylacetate (70 g), in the presence of triethylamine (47 g), in methylene chloride (470 cc) at a temperature of about 20° C. for 2 hours. After hydrolysis with distilled water (470 cc), the organic phase is washed with a 1 N aqueous solution of hydrochloric acid (250 cc) and then with distilled water (4×175 cc), dried over magnesium sulphate, in the presence of decolorising charcoal, and filtered, and the filtrate is concentrated to dryness under reduced pressure (20 mm Hg; 2.7 kPa) at 40° C. This gives ethyl 3-(N-methylcyclohexylamino)-3-oxopropionate (97 g) in the form of an orange oil.

[Rf=0.59; chromatography on a thin layer of silica gel; solvent: ethyl acetate].

EXAMPLE 8

Methyl iodide (10.65 g) is added to a suspension of 5-(pyrrolidin-1-yl)-1,2-dithiol-3-thione (10.51 g) in acetone (200 cc), and the reaction mixture is heated under reflux for 2 hours. After cooling to a temperature of about 20° C., the insoluble product is filtered off and washed with acetone (2×30 cc). After recrystallisation of the resulting product from water (200 cc), N-(5-methylthio-1,2-dithiol-3-ylidene)-pyrrolidinium iodide (14.8 g), melting at 197° C., is obtained.

5-(Pyrrolidin-1-yl)-1,2-dithiol-3-thione can be prepared by reacting phosphorus pentasulphide (287.5 g) with ethyl 3-(pyrrolidin-1-yl)-3-oxopropionate (160 g) in pyridine (1,600 cc) under reflux for 1 hour. After cooling to a temperature of about 20° C., the reaction mixture is hydrolysed with distilled water (11 liters) and extracted with methylene chloride (successively 1,600 cc and then 3×500 cc). The methylene chloride phases are combined, washed with distilled water (3×500 cc), dried over magnesium sulphate, in the presence of decolorising charcoal, and filtered, and the filtrate is concentrated to dryness under reduced pressure (20 mm Hg; 2.7 kPa) at 40° C. The residue is taken up in methylene chloride (100 cc) and the insoluble product is filtered off and washed with methylene chloride (30 cc). After drying, 5-(pyrrolidin-1-yl)-1,2-dithiol-3-thione (29 g), melting at 230° C., is thus obtained.

Ethyl 3-(pyrrolidin-1-yl)-3-oxopropionate can be prepared by reacting pyrrolidine (94.4 g) with ethyl chloroformylacetate (200 g), in the presence of triethylamine (134.4 g), methylene chloride (1,340 cc) at a temperature of about 20° C. for 2 hours. After hydrolysis with distilled water (1,340 cc), the organic phase is washed successively with a 1 N aqueous solution of hydrochloric acid (1,100 cc) and distilled water (3×1,100 cc), dried over magnesium sulphate and filtered, and the filtrate is concentrated to dryness under reduced pressure (20 mm Hg; 2.7 kPa) at 40° C. This gives ethyl 3-(pyrrolidin-1-yl)-3-oxopropionate (206.2 g) in the form of an orange oil.

[Rf=0.37; chromatography on a thin layer of silica gel; solvent: ethyl acetate].

EXAMPLE 9

A solution of iodoethane (3.46 g) in acetone (8 cc) is added dropwise, in the course of 20 minutes, to a suspension of 5-(pyrrolidin-1-yl)-1,2-dithiol-3-thione (3 g) in acetone (52 cc) under reflux, and the reaction mixture is then kept under reflux for 24 hours. After cooling to a temperature of about 20° C., the insoluble product formed is filtered off and washed with acetone (3×10 cc) and then with diisopropyl ether (2×10 cc).

By recrystallisation of the resulting product from ethanol (92 cc), N-(5-ethylthio-1,2-dithiol-3-ylidene)- pyrrolidinium iodide (4.5 g), melting at 165° C., is obtained.

EXAMPLE 10

A solution of 1-bromopropane (2.52 g) in acetone (5 cc) is added dropwise, in the course of 10 minutes, to a suspension of 5-(pyrrolidin-1-yl)-1,2-dithiol-3-thione (2.8 g) and sodium iodide (3.3 g) in acetone (37 cc) under reflux, and the reaction mixture is kept under reflux for 24 hours. The insoluble product formed is filtered off hot and washed successively with acetone (5 cc), with distilled water (2×5 cc) and then with acetone (2×5 cc).

By recrystalliation of the resulting product from ethanol (34 cc), N-(5-propylthio-1,2-dithiol-3-ylidene)-pyrrolidinium iodide (3.96 g), melting at 148° C., is obtained.

EXAMPLE 11

A solution of 1-iodoheptane (4.18 g) in acetone (7 cc) is added dropwise, in the course of 20 minutes, to a suspension of 5-(pyrrolidin-1-yl)-1,2-dithiol-3-thione (2.5 g) in acetone (43 cc) under reflux, and the reaction mixture is kept under reflux for 30 hours. After cooling to a temperature of about 20° C., the insoluble product formed is filtered off and washed with acetone (3×5 cc), with carbon disulphide (4×5 cc) and then with diethyl ether (2×5 cc).

By recrystallisation of the resulting product from propan-1-ol (50 cc), N-(5-heptylthio-1,2-dithiol-3-ylidene)-pyrrolidinium iodide (4.3 g), melting at 122° C., is obtained.

EXAMPLE 12

A solution of 2-iodoethanol (3.76 g) in acetone (10 cc) is added dropwise, in the course of 5 minutes, to a suspension of 5-(pyrrolidin-1-yl)-1,2-dithiol-3-thione (3.04 g) in acetone (50 cc) under reflux, and the reaction mixture is kept under reflux for 37 hours. After cooling to a temperature of about 20° C., the insoluble product formed is filtered off and washed with acetone (20 cc).

By recrystallisation of the resulting product from ethanol (300 cc), N-[5-(2-hydroxyethyl)-thio-1,2-dithiol-3-ylidene]-pyrrolidinium iodide (5.1 g), melting at 160°-162° C., is obtained.

EXAMPLE 13

Sodium iodide (7.41 g) is added to a suspension of 5-(pyrrolidin-1-yl)-1,2-dithiol-3-thione (6.1 g) in acetone (95 cc) under reflux, and a solution of phenacyl bromide (8.41 g) in acetone (25 cc) is then added dropwise. The reaction mixture is kept under reflux for 1 hour and then cooled to a temperature of about 20° C. The insoluble product formed is filtered off and washed successively with acetone (30 cc), distilled water (2×40 cc) and acetone (2×30 cc). The crude product obtained is recrystallised from a mixture of distilled water (215 cc) and ethanol (215 cc) and then stirred for 15 minutes in the presence of distilled water (200 cc) at a temperature of about 60° C. After filtration and drying, N-(5-phenacylthio-1,2-dithiol-3-ylidene)pyrrolidinium iodide (10.9 g), melting point at 179°-180° C., is obtained.

EXAMPLE 14

A solution of chloroacetone (2.12 g) in acetone (5 cc) is added to a suspension of 5-(pyrrolidin-1-yl)-1,2-dithiol-3-thione (3.04 g) and sodium iodide (3.75 g) in acetone (45 cc) under reflux, and reflux is maintained for 1 hour. After cooling to a temperature of about 20° C., the insoluble product formed is filtered off and washed with acetone (15 cc), with distilled water (4×25 cc) and then with acetone (30 cc).

By recrystallisation of the resulting product from a mixture of ethanol (1600 cc) and distilled water (50 cc), N-[5-(2-oxopropyl)thio-1,2-dithiol-3-ylidene]-pyrrolidinium iodide (3.6 g), melting at 200°-205° C., is obtained.

EXAMPLE 15

A solution of ethyl bromoacetate (5 g) in acetone (10 cc) is added to a suspension of 5-(pyrrolidin-1-yl)-1,2-dithiol-3-thione (4.06 g) and sodium iodide (4.8 g) in acetone (50 cc) under reflux, and the reaction medium is then kept under reflux for 18 hours. After cooling to a temperature of about 10° C., the insoluble product formed is filtered off and washed successively with acetone (15 cc), with distilled water (4×20 cc) and then with acetone (2×15 cc).

By recrystallisation of the resulting product from ethanol (200 cc), N-(5-ethoxycarbonylmethylthio-1,2-dithiol-3-ylidene)-pyrrolidinium iodide (6.8 g), melting at 168°-170° C., is obtained.

EXAMPLE 16

Sodium iodide (3 g) is added to a suspension of 5-(pyrrolidin-1-yl)-1,2-dithiol-3-thione (2.5 g) and chloroacetamide (1.7 g) in acetone (44 cc) under reflux, and reflux is maintained for 1 hour 30 minutes. After cooling at a temperature of about 20° C., the insoluble product formed is filtered off and washed successively with acetone (3×8 cc), distilled water (3×10 cc), carbon disulphide (2×10 cc) and diisopropyl ether (2×10 cc).

By recrystallisation of the resulting product from distilled water (44 cc), N-(5-carbamoylmethylthio-1,2-dithiol-3-ylidene)-pyrrolidinium iodide (4 g), melting at 222° C., is obtained.

EXAMPLE 17

A solution of chloroacetonitrile (1.38 g) in acetone (10 cc) is added to a suspension of 5-(pyrrolidin-1-yl)-1,2-dithiol-3-thione (2.5 g) and sodium iodide (3 g) in acetone (34 cc) under reflux, and the reaction mixture is kept under reflux for 20 hours. After cooling to a temperature of about 20° C., the insoluble product formed is filtered off and washed successively with acetone (3×5 cc), with distilled water (3×5 cc) and then with acetone (3×5 cc).

By recrystallisation of the resulting product from distilled water (60 cc), N-(5-cyanomethylthio-1,2-dithiol-3-ylidene)-pyrrolidinium iodide (3.25 g), melting at 191° C., is obtained.

EXAMPLE 18

Triethylamine (4.35 g) is added dropwise, in the course of 5 minutes, to a suspension of 2-diethylamino-1-chloroethane hydrochloride (7.4 g), 5-(pyrrolidin-1-yl)-1,2-dithiol-3-thione (4.45 g) and sodium iodide (9.9 g) in a mixture of acetone (110 cc) and dimethylformamide (25 cc) under reflux, and the reaction mixture is kept under reflux for 6 hours and then filtered at a temperature of about 50° C. in order to separate the insoluble product formed.

By recrystallisation of the resulting product from ethanol (250 cc), N-[5-(2-diethylaminoethyl)-thio-1,2-dithiol-3-ylidene]-pyrrolidinium iodide hydrochloride (2.4 g), melting at 200°-204° C., is obtained.

EXAMPLE 19

A solution of allyl bromide (2.66 g) in acetone (10 cc) is added dropwise, in the course of 10 minutes, to a suspension of 5-(pyrrolidin-1-yl)-1,2-dithiol-3-thione (3 g) and sodium iodide (3.6 g) in acetone (43 cc) under reflux, and the reaction mixture is kept under reflux for 1 hour. After cooling to a temperature of about 20° C., the insoluble product formed is filtered off and then washed with acetone (3×10 cc), distilled water (4×10 cc) and diethyl ether (3×10 cc).

By recrystallisation of the resulting product from ethanol (96 cc), N-(5-allylthio-1,2-dithiol-3-ylidene)-pyrrolidinium iodide (3.36 g), melting at 160° C., is obtained.

EXAMPLE 20

A solution of triethylamine (2.28 g) in acetone (25 cc) is added dropwise, in the course of 5 minutes, to a suspension of 2-chloromethylpyridine hydrochloride (3.7 g), 5-(pyrrolidin-1-yl)-1,2-dithiol-3-thione (3.04 g) and sodium iodide (6.75 g) in a mixture of acetone (50 cc) and dimethylformamide (15 cc) under reflux, and the reaction mixture is kept under reflux for 3 hours. After cooling to a temperature of about 20° C., the insoluble product formed is filtered off and washed successively with acetone (2×15 cc), distilled water (2×10 cc) and acetone (1×15 cc).

By recrystallisation of the resulting product from ethanol (110 cc), N-[5-(pyrid-2-yl)methylthio-1,2-dithiol-3-ylidene]-pyrrolidinium iodide (2 g), melting at 162°–163° C., is obtained.

EXAMPLE 21

A solution of 3-chloromethylpyridine (2.5 g) in acetone (7 cc) is added dropwise, in the course of 15 minutes, to a suspension of 5-(pyrrolidin-1-yl)-1,2-dithiol-3-thione (2.5 g) and sodium iodide (3 g) in acetone (37 cc) under reflux, and the reaction mixture is kept under reflux for 1 hour 30 minutes. After cooling to a temperature of about 20° C., the insoluble product formed is filtered off and washed successively with acetone (3×5 cc), distilled water (2×5 cc) and diisopropyl ether (2×5 cc).

By recrystallisation of the resulting product from distilled water (73 cc), N-[5-(pyrid-3-yl)-methylthio-1,2-dithiol-3-ylidene]-pyrrolidinium iodide (3.5 g), melting at 178° C., is obtained.

EXAMPLE 22

A suspension of 5-(pyrrolidin-1-yl)-1,2-dithiol-3-thione (2 g), 4-chloromethylpyridine hydrochloride (2.4 g) and sodium iodide (2.2 g) in acetone (36 cc) is heated under reflux for 2 hours. After cooling to a temperature of about 20° C., the insoluble product formed is filtered off and washed with acetone (3×10 cc) and then with carbon disulphide (3×10 cc).

By recrystallisation of the resulting product from ethanol (480 cc), N-[5-(pyrid-4-yl)methylthio-1,2-dithiol-3-ylidene]-pyrrolidinium iodide hemihydroiodide (2.8 g), melting at about 170° C., is obtained.

EXAMPLE 23

Triethylamine (5.25 cc) is added to a suspension of 5-dimethylamino-1,2-dithiol-3-thione (4.45 g), 3-chloromethylpyridine hydrochloride (6.15 g) and sodium iodide (11.25 g) in a mixture of acetone (125 cc) and dimethylformamide (25 cc). The reaction mixture is heated under reflux for 6 hours and then filtered whilst boiling. The insoluble product formed is collected and washed successively with acetone (40 cc), water (40 cc) and acetone (2×25 cc).

By recrystallisation of the resulting product from water (45 cc), N-[5-(pyrid-3-yl)methylthio-1,2-dithiol-3-ylidene]-dimethylammonium iodide (3.4 g), melting at 185° C., is obtained.

EXAMPLE 24

A solution of methyl iodide (6.4 g) in acetone (10 cc) is added to a suspension of 5-(piperidin-1-yl)-1,2-dithiol-3-thione (3.26 g) in acetone (50 cc) under reflux, and the reaction mixture is kept under reflux for 2 hours. After cooling to a temperature of about 20° C., the insoluble product formed is filtered off and washed with acetone (10 cc).

By recrystallisation of the resulting product from ethanol (50 cc), N-(5-methylthio-1,2-dithiol-3-ylidene)-piperidinium iodide (3.9 g), melting at 149°–150° C., is obtained.

5-(Piperidin-1-yl)-1,2-dithiol-3-thione can be prepared by reacting phosphorus pentasulphide (127 g) with ethyl 3-(piperidin-1-yl)-3-oxopropionate (71 g) in pyridine (720 cc) under reflux for 1 hour. The reaction mixture is then cooled to a temperature of about 20° C., diluted with water (6 liters) and extracted with methylene chloride (6×500 cc). The organic phases are combined, washed with distilled water (3×500 cc), dried over magnesium sulphate and filtered, and the filtrate is concentrated to dryness under reduced pressure (20 mm Hg; 2.7 kPa) at 40° C. The residue obtained is taken up in dimethylformamide (90 cc) and the insoluble product is filtered off and washed with dimethylformamide (5 cc) and then with diethyl ether (2×15 cc).

By recrystallisation of the resulting product from acetonitrile (600 cc), 5-(piperidin-1-yl)-1,2-dithiol-3-thione (9.5 g), melting at 194° C., is obtained.

Ethyl 3-(piperidin-1-yl)-3-oxopropionate can be prepared by reacting piperidine (34 g) with ethyl chloroformylacetate (60 g), in the presence of triethylamine (40.4 g), in methylene chloride (400 cc) at a temperature of about 20° C. for 3 hours. After hydrolysis with water (400 cc), the organic phase is washed successively with a 1 N aqueous solution of hydrochloric acid (400 cc), with distilled water (2×400 cc), with a 2% aqueous solution of sodium bicarbonate (400 cc) and then with distilled water (400 cc), dried over magnesium sulphate and filtered, and the filtrate is concentrated to dryness under reduced pressure (20 mm Hg; 2.7 kPa) at 40° C. This gives ethyl 3-(piperidin-1-yl)-3-oxopropionate (71 g) in the form of an orange oil.

[Rf=0.45; chromatography on a thin layer of silica gel; solvent: ethyl acetate].

EXAMPLE 25

A solution of methyl iodide (2.31 g) in acetone (6 cc) is added to a solution of 5-(perhydroazepin-1-yl)-1,2-dithiol-3-thione (2.5 g) in acetone (38 cc) under reflux, and the reaction mixture is kept under reflux for 1 hour. After cooling to a temperature of about 20° C., the insoluble product formed is filtered off and washed successively with acetone (3×55 cc), carbon disulphide (2×5 cc) and diethyl ether (2×5 cc).

By recrystallisation of the resulting product from ethanol (16 cc), N-(5-methylthio-1,2-dithiol-3-ylidene)-perhydroazepinium iodide (3.6 g), melting at 130° C., is obtained.

5-(Perhydroazepin-1-yl)-1,2-dithiol-3-thione can be prepared by reacting phosphorus pentasulphide (91.4 g) with ethyl 3-(perhydroazepin-1-yl)-3-oxopropionate (59 g) in pyridine (680 cc) under reflux for 1 hour. The reaction mixture is then cooled to a temperature of about 20° C., diluted with distilled water (6860 cc) and extracted with methylene chloride (780 cc and then 2×560 cc). The organic phases are combined, washed successively with 4 N ammonia solution (3×370 cc) and then with distilled water (370 cc), dried over magnesium sulphate and filtered, and the filtrate is concentrated to dryness under reduced pressure (20 mm Hg; 2.7 kPa) at 40° C. The residue is taken up in acetonitrile (25 cc); the insoluble product is filtered off and washed with acetonitrile (3×10 cc). The product thus obtained is dissolved in methylene chloride (50 cc) and the resulting solution is poured onto silica gel (200 g) contained in a column of diameter 4 cm. Elution is carried out first with methylene chloride (900 cc); the corresponding eluate is discarded. Elution is then carried out with methylene chloride (6100 cc); the corresponding eluate is concentrated to dryness under reduced pressure (20 mm Hg; 2.7 kPa) at 40° C. This gives 5-(perhydroazepin-1-yl)-1,2-dithiol-3-thione (8.1 g), melting at 120° C.

Ethyl 3-(perhydroazepin-1-yl)-3-oxopropionate can be prepared by reacting perhydroazepine (33 g) with ethyl chloroformylacetate (50 g) in the presence of triethylamine (33.6 g), in methylene chloride (333 cc) at a temperature of about 20° C. for 2 hours. After hydrolysis with distilled water (333 cc), the organic phase is washed successively with a 1 N aqueous solution of hydrochloric acid (270 cc), distilled water (250 cc and then 2×120 cc), a 0.4% aqueous solution of sodium bicarbonate (260 cc) and distilled water (250 cc), dried over magnesium sulphate, in the presence of decolorising charcoal, and filtered, and the filtrate is concentrated to dryness under reduced pressure (20 mm Hg; 2.7 kPa) at 40° C. This gives ethyl 3-(perhydroazepin-1-yl)-3-oxo-propionate (60 g) in the form of an orange oil.

[Rf=0.63; chromatography on a thin layer of silica gel; solvent: ethyl acetate].

EXAMPLE 26

A solution of methyl iodide (9.35 g) in acetone (20 cc) is added to a suspension of 5-morpholino-1,2-dithiol-3-thione (4.8 g) in acetone (80 cc) under reflux, and the reaction mixture is kept under reflux for 3 hours. After cooling to a temperature of about 10° C., the insoluble product formed is filtered off and washed with acetone (20 cc).

By recrystallisation of the resulting product from a mixture of ethanol (50 cc) and distilled water (50 cc), N-(5-methylthio-1,2-dithiol-3-ylidene)morpholinium iodide (7.2 g), melting at 228°-230° C., is obtained.

5-Morpholino-1,2-dithiol-3-thione can be prepared by reacting phosphorus pentasulphide (53.6 g) with ethyl 3-morpholino-3-oxopropionate (30 g) in pyridine (300 cc) under reflux for 1 hour. The reaction mixture is then cooled to a temperature of about 20° C., hydrolysed with water (3 liters) and extracted with methylene chloride (500 cc). The insoluble product formed is filtered off, washed with diisopropyl ether (2×20 cc) and dried. This gives 5-morpholino-1,2-dithiol-3-thione (3.1 g) melting at 248°-250° C. The filtrate is then washed with distilled water (4×300 cc), dried over magnesium sulphate and filtered, and the filtrate is concentrated to dryness under reduced pressure (20 mm Hg; 2.7 kPa) at 40° C. The residue obtained is taken up in dimethylformamide (30 cc) and the insoluble product formed is filtered off and washed with dimethylformamide (5 cc) and then with methylene chloride (2×5 cc). After drying, a further batch of 5-morpholino-1,2-dithiol-3-thione (2 g), melting at 248°-250° C., is obtained.

Ethyl 3-morpholino-3-oxopropionate can be prepared by reacting morpholine (17.4 g) with ethyl chloroformylacetate (30.1 g), in the presence of triethylamine (20.2 g), in methylene chloride (200 cc) at a temperature of about 20° C. for 2 hours 30 minutes. After hydrolysis with distilled water (200 cc), the organic phase is washed successively with distilled water (200 cc), with a 1 N aqueous solution of hydrochloric acid (200 cc), with distilled water (2×200 cc), with a 2% aqueous solution of sodium bicarbonate (200 cc) and then with distilled water (200 cc), dried over magnesium sulphate and filtered, and the filtrate is concentrated to dryness under reduced pressure (20 mm Hg; 2.7 kPa) at 40° C. This gives ethyl 3-morpholino-3-oxopropionate (30 g), melting at 60° C.

EXAMPLE 27

Chloroacetamide (2.8 g) and sodium iodide (4.95 g) are added to a solution of 5-morpholino-1,2-dithiol-3-thione (4.02 g) in acetone (80 cc), and the reaction mixture is heated under reflux for 3 hours. After cooling to a temperature of about 20° C., the insoluble product formed is filtered off and washed successively with acetone (20 cc), distilled water (3×20 cc) and acetone (40 cc).

After recrystallisation of the product from a mixture of ethanol (480 cc) and distilled water (120 cc), N-(5-carbamoylmethylthio-1,2-dithiol-3-ylidene)-morpholinium iodide (4.3 g), melting at 244°-247° C., is obtained.

EXAMPLE 28

A solution of methyl iodide (4.25 g) in acetone (5 cc) is added to a solution of 5-phenylamino-1,2-dithiol-3-thione (3.4 g) in acetone (30 cc) under reflux, and reflux is maintained for 1 hour. After cooling to a temperature of about 20° C., the insoluble product formed is filtered off and washed with acetone (5 cc).

By recrystallisation of the resulting product from ethanol (300 cc), 5-methylthio-3-phenylimino-1,2-dithiole hydroiodide (4 g), melting at 164°-165° C., is obtained.

5-Phenylamino-1,2-dithiol-3-thione can be prepared by reacting ethyl 3-phenylamino-3-oxopropionate (90 g) with phosphorus pentasulphide (146 g) in dioxan (900 cc) under reflux for 20 minutes. After cooling to a temperature of about 20° C., the reaction mixture is poured into a mixture of water (5.5 liters), concentrated ammonia solution (d=0.92; 650 cc) and methylene chloride (1.5 liters). The resulting mixture is stirred for 20 minutes. The aqueous phase is then decanted and washed with methylene chloride (2×700 cc). The methylene chloride phases are combined, dried over sodium sulphate and filtered, and the filtrate is concentrated to dryness under reduced pressure (20 mm Hg; 2.7 kPa) at 40° C. The residue obtained is taken up in methylene chloride (65 cc); the insoluble product is filtered off and then washed with methylene chloride (4×15 cc) and diisopropylether (2×20 cc). This gives 5-phenylamino-1,2-dithiol-3-thione (19 g) melting at 135° C.

Ethyl 3-phenylamino-3-oxopropionate can be prepared in accordance with the method described by F. D. Chattaway et al., J. Chem. Soc. 97, 939 (1910).

EXAMPLE 29

A solution of 5-phenylamino-1,2-dithiol-3-thione (9 g), chloroacetic acid (4.15 g) and sodium iodide (6.6 g) in acetone (135 cc) is heated under reflux for 35 minutes. After cooling to a temperature of about 20° C., the insoluble product is filtered off and washed successively with acetone (3×15 cc), with water (3×10 cc) and then with acetone (3×10 cc). By recrystallisation of this crude product from methanol (470 cc), (3-phenylimino-1,2-dithiol-5-ylthio)-acetic acid hydroiodide (7.1 g) is obtained, melting at about 205° C. with decomposition.

The corresponding base can be prepared in the following manner:

The hydroiodide obtained as described above is suspended in distilled water (70 cc). Sodium bicarbonate (2.93 g) is added to this suspension: this gives a solution of pH 7, containing a very small amount of insoluble material, which is filtered off. The filtrate obtained is then acidified to pH 5 by adding a 1 N aqueous solution of hydrochloric acid (16.5 cc). The product which precipitates is filtered off and then washed with water (9×10 cc). After drying, (3-phenylimino-1,2-dithiol-5-ylthio)-acetic acid (3.7 g), melting at 147° C., is obtained.

EXAMPLE 30

Ethyl bromoacetate (4.5 g) is added to a solution of 5-phenylamino-1,2-dithiol-3-thione (4 g) in acetone (70 cc), and the reaction mixture is heated under reflux for 24 hours. After cooling to a temperature of about 20° C., the insoluble product formed is filtered off and washed with acetone (3×5 cc). The filtrates are combined and concentrated to dryness under reduced pressure (20 mm Hg; 2.7 kPa) at 40° C., and the residue is taken up in ethanol (15 cc). The insoluble product is filtered off and washed with ethanol (3×10 cc) and then with diethyl ether (2×10 cc).

By recrystallisation of the resulting product from methyl ethyl ketone (36 cc), ethyl (3-phenylimino-1,2-dithiol-5-ylthio)-acetate hydrobromide (2.8 g), melting at 90° C., is obtained.

EXAMPLE 31

Chloroacetamide (2.15 g) and sodium iodide (3.75 g) are added to a solution of 5-phenylamino-1,2-dithiol-3-thione (3.4 g) in acetone (60 cc). The reaction mixture is heated under reflux for 1 hour. After cooling to a temperature of about 20° C., the insoluble product formed is filtered off and washed successively with acetone (20 cc), distilled water (3×20 cc) and acetone (20 cc).

By recrystallisation of the resulting product from ethanol (500 cc), (3-phenylimino-1,2-dithiol-5-ylthio)-acetamide hydroiodide (3.5 g), melting at 174°–175° C., is obtained.

EXAMPLE 32

A solution of 5-phenylamino-1,2-dithiol-3-thione (13.5 g), dimethylcarbamoyl chloride (7.08 g) and sodium iodide (9.9 g) in anhydrous acetone (205 cc) is heated under reflux for 24 hours. After cooling to a temperature of about 20° C., the insoluble product formed is filtered off and washed successively with acetone (3×25 cc) and then with water (3×25 cc). This gives 5-dimethylcarbamoylthio-3-phenylimino-1,2-dithiole hydroiodide (12.1 g) melting at 214° C.

The corresponding base can be prepared in the following manner:

The salt obtained as described above is suspended in water (120 cc). Sodium bicarbonate (2.9 g), followed by methylene chloride (250 cc), are then added with stirring. After stirring for 20 minutes, the aqueous phase is decanted and washed with methylene chloride (50 cc). The methylene chloride phases are combined, dried over sodium sulphate and filtered, and the filtrate is concentrated to dryness under reduced pressure (20 mm Hg; 2.7 kPa) at 40° C.

By recrystallisation of the resulting residue from acetonitrile (55 cc), 5-dimethylcarbamoylthio-3-phenylimino-1,2-dithiole (8 g), melting at 134° C., is obtained.

EXAMPLE 33

Triethylamine (16.2 g) and then anhydrous pyridine (32 cc) are added dropwise, with stirring and in the course of 15 minutes, to a suspension of 5-phenylamino-1,2-dithiol-3-thione (9 g) and 1-chlorocarbonyl-4-methylpiperazine hydrochloride (23.9 g) in anhydrous methylene chloride (90 cc), kept at a temperature of about 20° C. The reaction mixture is then heated under reflux for 3 hours. After cooling to a temperature of about 20° C., the reaction mixture is poured into water (400 cc) and the aqueous phase is decanted and washed with methylene chloride (2×100 cc). The methylene chloride phases are conbined, washed with distilled water (4×100 cc), dried over sodium sulphate and filtered, and the filtrate is concentrated to dryness under reduced pressure (20 mm Hg; 2.7 kPa) at 40° C. The residue obtained is taken up in acetone (20 cc); the insoluble product is filtered off and then washed with with acetone (3×6 cc).

By recrystallisation of the resulting product from acetonitrile (235 cc), 5-(4-methylpiperazin-1-yl)-carbonylthio-3-phenylimino-1,2-dithiole (8.3 g), melting at 146° C., is obtained.

EXAMPLE 34

Sodium iodide (3.3 g) and then N-chlorocarbonyl-morpholine (3.6 g) are added to a suspension of 5-phenylamino-1,2-dithiol-3-thione (3 g) in acetone (53 cc). The reaction mixture is heated under reflux for 20 hours. After cooling to a temperature of about 20° C., the insoluble product formed is filtered off and then washed successively with acetone (2×10 cc), distilled water (4×10 cc) and diethyl ether (3×10 cc). By recrystallisation of the resulting product from a mixture of ethanol (80 cc) and distilled water (80 cc), a mixture of 5-morpholinocarboxylthio-3-phenylimino-1,2-dithiol hydroiodide and hydrochloride (4.4 g) is obtained melting at about 140° C. A suspension of the resulting mixture of salts in a mixture of methylene chloride (60 cc) and distilled water (40 cc), to which sodium bicarbonate (1 g) has been added, is stirred for 30 minutes. The organic phase is separated by decantation and the aqueous phase is washed with methylene chloride (60 cc). The methylene chloride phases are combined and washed with distilled water (40 cc), dried over magnesium sulphate, in the presence of decolorising charcoal, and filtered, and the filtrate is concentrated to dryness under reduced pressure (20 mm Hg; 2.7 kPa) at 40° C.

By recrystallisation of the resulting product from ethanol (250 cc), 5-morpholinocarbonylthio-3-phenylimino-1,2-dithiole (2.76 g), melting at 162° C., is obtained.

EXAMPLE 35

A solution of 5-phenethylamino-1,2-dithiol-3-thione (11.3 g) and methyl iodide (12.8 g) in acetone (225 cc) is obtained under reflux for 1 hour. After cooling to a temperature of about 20° C., the insoluble product formed is filtered off, washed with acetone (2×20 cc) and then dried. By recrystallisation of the resulting crude product from water (730 cc), 3-phenethylimino-5-methylthio-1,2-dithiole hydroiodide (12.3 g), melting at 172° C., is obtained.

5-Phenethylamino-1,2-dithiol-3-thione can be prepared by reacting ethyl 3-phenethylamino-3-oxopropionate (80.9 g) with phosphorus pentasulphide (114 g) in dioxan (810 cc) under reflux for 1 hour. After cooling to a temperature of about 20° C., the reaction mixture is poured into a mixture of water (4 liters), concentrated ammonia solution (d=0.92; 0.7 liter) and methylene chloride (1.5 liters), and the resulting mixture is stirred for 20 minutes. The aqueous phase is then decanted and washed with methylene chloride (1 liter). The methylene chloride phases are combined, dried over sodium sulphate and filtered, and the filtrate is concentrated to dryness under reduced pressure (20 mm Hg; 2.7 kPa) at 40° C. The residue obtained is dissolved in a methylene chloride/cyclohexane mixture (50/50 by volume; 1.4 liters) and the solution obtained is poured into silica gel (1,400 g) contained in a column of diameter 9 cm. Elution is carried out with a methylene chloride/cyclohexane mixture (50/50 by volume; 7 liters) and then with pure methylene chloride (10 liters). These eluates are discarded. Elution is then carried out with pure methylene chloride (15 liters) and then with a methylene chloride/methanol mixture (99/1 by volume; 3 liters). These eluates are combined and concentrated to dryness under reduced pressure (20 mm Hg; 2.7 kPa) at 40° C. This gives 5-phenethylamino-1,2-dithiol-3-thione (27 g) in the form of a brown oil.

[Rf=0.14; chromatography on a thin layer of silica gel; solvent: methylene chloride].

Ethyl 3-phenethylamino-3-oxopropionate can be prepared by reacting phenethylamine (42.3 g) with ethyl chloroformylacetate (52.7 g) in anhydrous methylene chloride (425 cc), in the presence of triethylamine (35.4 g), for 2 hours 30 minutes at a temperature of about 20° C. Water (250 cc) is then added to the reaction mixture, and the methylene chloride phase is then decanted and washed successively with a 1 N aqueous solution of hydrochloric acid (250 cc), water (250 cc), a 1 N aqueous solution of sodium hydroxide (250 cc) and water (3×250 cc). After drying over sodium sulphate, the methylene chloride phase is filtered and the filtrate is concentrated to dryness under reduced pressure (20 mm Hg; 2.7 kPa) at 40° C. This gives ethyl 3-phenethylamino-3-oxopropionate (67.9 g) melting at 60° C.

EXAMPLE 36

A solution of methyl iodide (4.25 g) in acetone (5 cc) is added to a solution of 5-ethylamino-1,2-dithiol-3-thione (1.9 g) in acetone (30 cc) under reflux, and the reaction mixture is kept under reflux for 2 hours 20 minutes. After cooling to a temperature of about 20° C., the insoluble product formed is filtered off and washed with acetone (10 cc).

After recrystallisation from ethanol (50 cc), 3-ethylimino-5-methylthio-1,2-dithiole hydroiodide (0.8 g), melting at 190° C., is obtained.

5-Ethylamino-1,2-dithiol-3-thione can be obtained by reacting ethyl 3-ethylamino-3-oxopropionate (65 g) with phosphorus pentasulphide (135 g) in pyridine (970 cc) under reflux for 3 hours. After cooling to a temperature of about 20° C., the reaction mixture is hydrolysed with distilled water (6 liters) and then extracted with methylene chloride (1 liter and then 3×500 cc). The methylene chloride phases are combined, washed with distilled water (3×800 cc), dried over magnesium sulphate and filtered, and the filtrate is concentrated to dryness under reduced pressure (20 mm Hg; 2.7 kPa) at 40° C. The residue is dissolved in methylene chloride (100 cc) and the solution is poured onto silica gel (2 kg) contained in a column of diameter 10 cm. Elution is carried out first with methylene chloride (18 liters); the corresponding eluate is discarded. Elution is then carried out with a mixture of methylene chloride and ethyl acetate (80/20 by volume; 3 liters); the corresponding eluate is concentrated to dryness under reduced pressure (20 mm Hg; 2.7 kPa) at 40° C. This gives 5-ethylamino-1,2-dithiol-3-thione (2 g) in the form of a brown oil.

[Rf=0.70; chromatography on a thin layer of silica gel; solvent:ethyl acetate].

Ethyl 3-ethylamino-3-oxopropionate can be obtained by reacting ethylamine (27 g) with ethyl chloroformylacetate (90.5 g), in the presence of triethylamine (60.5 g), in methylene chloride (600 cc) at a temperature of about 20° C. for 4 hours. After hydrolysis with distilled water (400 cc), the reaction mixture is decanted and the methylene chloride phase is washed successively with distilled water (2×150 cc), with a 1 N aqueous solution of hydrochloric acid (100 cc) and then with distilled water (2×150 cc). The organic phase is then dried over magnesium sulphate and filtered, and the filtrate is concentrated to dryness under reduced pressure (20 mm Hg; 2.7 kPa) at 40° C. This gives ethyl 3-ethylamino-3-oxopropionate (65 g) melting at 40° C.

EXAMPLE 37

N,N-Dimethylchloroacetamide (3.7 g) is added to a suspension of 5-(pyrrolidin-1-yl)-1,2-dithiol-3-thione (4.06 g) and sodium iodide (4.9 g) in acetone (70 cc), and the reaction mixture is kept under reflux for 1 hour. After cooling, the insoluble product is filtered off and washed successively with acetone (3×20 cc), with water (3×20 cc) and then with diethyl ether (3×20 cc). The product obtained is then recrystallised once from methanol (150 cc) and then a second time from ethanol (340 cc). This gives N-[5-dimethylcarbamoylmethylthio-1,2-dithiol-3-ylidene]-pyrrolidinium iodide (4.8 g) melting at 152° C.

EXAMPLE 38

3-Bromoacetylpyridine hydrobromide (6.38 g) is added to a suspension of 5-(pyrrolidin-1-yl)-1,2-dithiol-3-thione (3 g) and sodium iodide (3.3 g) in acetone (54 cc), and the reaction mixture is kept under reflux for 12 hours. After cooling to a temperature of about 20° C., the insoluble product is filtered off and washed successively with acetone (3×20 cc) and then with distilled water (10 cc). By recrystallisation of the resulting product from methanol (100 cc), [5-(pyrid-3-yl)carbonylmethylthio-1,2-dithiol-3-ylidene]pyrrolidinium bromide hydrobromide (3.55 g), melting at 155° C. with decomposition, is obtained.

EXAMPLE 39

A solution of phenacyl bromide (3.98 g) in acetone (10 cc) is added, in the course of 5 minutes, to a solution of 5-anilino-1,2-dithiol-3-thione (3 g) and sodium iodide (3.3 g) in acetone (50 cc) under reflux, and reflux is maintained for 1 hour with stirring. After cooling to a temperature of about 20° C., the insoluble product formed is filtered off and washed successively with acetone (2×10 cc), with distilled water (3×10 cc) and then with diethyl ether (2×10 cc).

By recrystallisation of the resulting product from a 50/50 mixture of distilled water and ethanol (600 cc), 5-phenacylthio-3-phenylimino-1,2-dithiole hydroiodide (3.5 g), melting at 180° C., is obtained.

The corresponding base can be prepared in the following manner:

The salt obtained as described above is suspended in distilled water (32 cc). Sodium bicarbonate (0.84 g) and methylene chloride (50 cc) are then added with stirring. After stirring for 5 minutes, the organic phase is decanted, washed with distilled water (32 cc), dried over magnesium sulphate in the presence of decolorising charcoal, and filtered, and the filtrate is concentrated to dryness under reduced pressure (20 mm Hg; 2.7 kPa) at 40° C.

By recrystallisation of the resulting residue from ethanol (60 cc), 5-phenacylthio-3-phenylimino-1,2-dithiole (2.03 g), melting at 110° C., is obtained.

EXAMPLE 40

4-Acetyl-1-chlorocarbonylpiperazine (9.15 g) is added to a solution of 5-anilino-1,2-dithiol-3-thione (6.46 g) and sodium iodide (6.6 g) in acetone (135 cc) under reflux, and reflux is maintained for 19 hours with stirring. After cooling to a temperature of about 20° C., the insoluble product formed is filtered off and washed successively with acetone (2×10 cc), distilled water (3×20 cc) and diethyl ether (2×10 cc). This gives 5-(4-acetylpiperazinyl)carbonylthio-3-phenylimino-1,2-dithiole hydroiodide (9.5 g) melting at 240° C.

The corresponding base can be prepared in the following manner:

The salt obtained as described above is suspended in distilled water (100 cc). Sodium bicarbonate (2.6 g) and methylene chloride (155 cc) are then added with stirring. After stirring for 5 minutes, the organic phase is decanted, washed with distilled water (100 cc), dried over magnesium sulphate in the presence of decolorising charcoal, and filtered, and the filtrate is concentrated to dryness under reduced pressure (20 mm Hg; 2.7 kPa) at 40° C.

By recrystallisation of the resulting residue from ethanol (700 cc), 5-(4-acetylpiperazinyl)carbonylthio-3-phenylimino-1,2-dithiole (5.9 g), melting at 193° C., is obtained.

EXAMPLE 41

Phenacyl chloride (10.5 g) is added to a suspension of 5-morpholino-1,2-dithiol-3-thione (9.85 g) in ethanol (200 cc), and the reaction mixture is kept under reflux for 3 hours. After cooling to a temperature of about 10° C., the insoluble product formed is filtered off and washed with ethanol (30 cc). After drying, N-(5-phenacylthio-1,2-dithiol-3-ylidene)-morpholinium chloride (14.3 g) is obtained, which melts at 138° C. and is solvated by 9% of ethanol.

The product thus prepared in the form of the chloride can be trans-salified to the hydrogensulphate in the following manner:

A solution of concentrated sulphuric acid (d=1.83; 0.2 cc) in ethanol (5 cc) is added to a solution of N-(5-phenacylthio-1,2-dithiol-3-ylidene)-morpholinium chloride (0.75 g) in ethanol (20 cc) under reflux. After cooling to a temperature of about 10° C., the insoluble product formed is filtered off and washed with ethanol (4 cc). After drying, N-(5-phenacylthio-1,2-dithiol-3-ylidene)-morpholinium hydrogensulphate (0.8 g), melting at 192° C., is obtained.

EXAMPLE 42

Sodium iodide (2.9 g) and dimethylcarbamoyl chloride (3.8 g) are added to a solution of 5-benzylamino-1,2-dithiol-3-thione (3.88 g) in acetone (65 cc) under reflux, and reflux is maintained for 45 hours. After cooling to a temperature of about 20° C., the insoluble product is filtered off and washed successively with acetone (2×15 cc), with distilled water (2×20 cc) and then with acetone (15 cc). This gives 3-benzylimino-5-dimethylcarbamoylthio-1,2-dithiole hydroiodide (6 g) melting at 205° C.

The corresponding base can be prepared in the following manner:

The salt obtained as described above is suspended in distilled water (59 cc). Sodium bicarbonate (1.53 g) and methylene chloride (92 cc) are then added with stirring. After stirring for 10 minutes, the organic phase is washed with distilled water (59 cc), dried over magnesium sulphate in the presence of decolorising charcoal, and filtered, and the filtrate is concentrated to dryness under reduced pressure (20 mg Hg; 2.7 kPa) at 40° C.

By recrystallisation of the resulting residue from ethanol (125 cc), 3-benzylimino-5-dimethylcarbamoylthio-1,2-dithiole (3.8 g), melting at 135° C., is obtained.

5-Benzylamino-1,2-dithiol-3-thione can be prepared by reacting phosphorus pentasulphide (26.4 g) with ethyl 3-benzylamino-3-oxopropionate (17.6 g) in dioxan (175 cc) under reflux for 30 minutes. After cooling to a temperature of about 70° C., the reaction mixture is hydrolysed with a 10% aqueous solution of ammonia (d=0.92; 400 cc) for 30 minutes, with stirring, and extracted with methylene chloride (2×100 cc). The combined organic phases are washed with distilled water (100 cc), dried over magnesium sulphate in the presence of decolorising charcoal, and filtered, and the filtrate is concentrated to dryness under reduced pressure (20 mm Hg; 2.7 kPa) at 50° C. The residue obtained is dissolved in methylene chloride (100 cc) and the solution obtained is poured onto silica gel (320 g) contained in a column of diameter 5 cm. Elution is carried out with methylene chloride (4.5 liters); the eluate is discarded. Elution is then carried out with methylene chloride (2 liters) and then with a methylene chloride/methanol mixture (99/1 by volume; 2 liters). These eluates are combined and concentrated to dryness under reduced pressure (20 mm Hg; 2.7 kPa) at 40° C. The residue thus obtained is taken up in methylene chloride (5 cc) and the insoluble product is filtered off and then washed with methylene chloride (2 cc). This gives 5-benzylamino-1,2-dithiol-3-thione (4g) melting at 130° C.

EXAMPLE 43

Sodium iodide (4.8 g) is added to a solution of 5-phenethylamino-1,2-dithiol-3-thione (6.9 g) in acetone (100 cc), and the mixture is heated to the reflux temperature. A solution of dimethylcarbamoyl chloride (6.4 g) in acetone (10 cc) is then added in the course of 5 minutes, and reflux is maintained for 45 hours. After cooling to a temperature of about 20° C., the insoluble product formed is filtered off and washed successively withe acetone (2×10 cc), with distilled water (2×10 cc) and then with acetone (10 cc). This gives 5-dimethylcarbamoylthio-3-phenethylimino-1,2-dithiolehydroiodide (7.85 g) melting at 198° C.

The corresponding base can be prepared in the following manner:

The salt obtained as described above is suspended in distilled water (75 cc). Sodium bicarbonate (1.95 g) and methylene chloride (120 cc) are then added with stirring. After stirring for 5 minutes, the organic phase is washed with distilled water (75 cc), dried over magnesium sulphate in the presence of decolorising charcoal, and filtered, and the filtrate is concentrated to dryness under reduced pressure (20 mm Hg; 2.7 kPa) at 40° C.

By recrystallisation of the resulting residue from ethanol (110 cc), 5-dimethylcarbamoylthio-3-phenethylimino-1,2-dithiole (4.8 g), melting at 115° C., is obtained.

EXAMPLE 44

2-Bromoacetylthiophene (6.15 g) is added to a suspension of 5-(pyrrolidin-1-yl)-1,2-dithiol-3-thione (4.06 g) and sodium iodide (4.9 g) in acetone (105 cc), and the reaction mixture is kept under reflux for 1½ hours. After cooling, the insoluble product is filtered off and washed successively with acetone (3×20 cc), with water (3×20 cc) and then with diethyl ether (3×20 cc). By recrystallisation of the resulting product from ethanol (4000 cc), N-[5-(then-2-oyl)methylthio-1,2-dithiol-3-ylidene]-pyrrolidinium iodide (4.9 g), melting at 197° C., is obtained.

EXAMPLE 45

A suspension of 5-morpholino-1,2-dithiol-3-thione (8 g), α-bromopropiophenone (11.63 g) and sodium iodide (9 g) in acetone (200 cc) is heated under reflux for 2½ hours. After cooling to a temperature of about 20° C., the insoluble product is filtered off and washed successively with acetone (3×20 cc), water (5×50 cc) and acetone (3×20 cc).

By recrystallisation of the resulting product from a mixture of ethanol (150 cc) and water (25 cc), N-[5-(α-methylphenacylthio)-1,2-dithiol-3-ylidene]-morpholinium iodide (9.5 g), melting at 163° C., is obtained.

EXAMPLE 46

A solution of 5-phenylamino-1,2-dithiol-3-thione (4.5 g), sodium iodide (4.5 g) and ethyl chloroformate (2.6 g) in anhydrous acetone (120 cc) is stirred for 65 hours at a temperature of about 20° C. The insoluble product formed is filtered off, washed successively with acetone (2×20 cc), with distilled water (3×30 cc) and then with acetone (2×20 cc) and dried under reduced pressure (20 mm Hg; 2.7 kPa) at 20° C.

By recrystallisation of the resulting product from ethanol (100 cc), 5-ethoxycarbonylthio-3-phenylimino-1,2-dithiolehydroiodide (3.6 g), melting at 112°–116° C., is obtained.

EXAMPLE 47

α-Bromo-γ-butyrolactone (4.9 g) is added to a suspension of 5-(pyrrolidin-1-yl)-1,2-dithiol-3-thione (4.06 g) and sodium iodide (4.9 g) in acetone (70 cc), and the reaction mixture is heated under reflux for 6 hours. After cooling, the insoluble product is filtered off and washed successively with acetone (3×20 cc), with water (3×20 cc) and then with diethyl ether (3×20 cc). By recrystallisation of the resulting product from methanol (235 cc), N-[5-(2-oxotetrahydrofuran-3-yl)thio-1,2-dithiol-3-ylidene]-pyrrolidinium iodide (5.6 g), melting at 180° C., is obtained.

EXAMPLE 48

A solution of dimethylcarbamoyl chloride (1.77 g) in acetone (10 cc) is added to a solution of 5-(3-methoxyphenyl)amino-1,2-dithiol-3-thione (3.85 g) and sodium iodide (2.7 g) in acetone (50 cc) under reflux. The reaction mixture is heated under reflux for 40 hours. After cooling to a temperature of about 20° C., the insoluble product formed is filtered off and washed successively with acetone (20 cc), distilled water (3×20 cc) and acetone (20 cc). This gives 5-dimethylcarbamoylthio-3-(3-methoxyphenyl)imino-1,2-dithiole hydroiodide (2.9 g) melting at 205° C.

The corresponding base can be prepared in the following manner:

The salt obtained as described above is suspended in water (50 cc). Sodium bicarbonate (0.6 g) and then methylene chloride (50 cc) are subsequently added with stirring. After stirring for 5 minutes, the aqueous phase is decanted and washed with methylene chloride (20 cc). The methylene chloride phases are combined, washed with distilled water (2×50 cc), dried over magnesium sulphate and filtered, and the filtrate is concentrated to dryness under reduced pressure (20 mm Hg; 2.7 kPa) at 40° C.

By recrystallisation of the resulting residue from ethanol (40 cc), 5-dimethylcarbamoylthio-3-(3-methoxyphenyl)imino-1,2-dithiole (1.5 g), melting at 104°–106° C., is obtained.

5-(3-Methoxyphenyl)amino-1,2-dithiol-3-thione can be prepared by reacting phosphorus pentasulphide (80 g) with ethyl 3-(3-methoxyphenylamino)-3-oxopropionate (56.5 g) in dioxan (550 cc) under reflux for 5 minutes. After cooling to a temperature of about 45° C., the reaction mixture is hydrolysed with a 10% aqueous solution of ammonia (d=0.92; 4 liters) for 15 minutes, with stirring, and extracted with methylene chloride (successively 5×500 cc). The methylene chloride phases are combined, washed with distilled water (3×500 cc), dried over magnesium sulphate in the presence of decolorising charcoal, and filtered, and the filtrate is concentrated to dryness under reduced pressure (20 mm Hg; 2.7 kPa) at 80° C. The residue is taken up in methylene chloride (30 cc) and the product which crystallises is filtered off and washed with methylene chloride (5 cc) and then with diethyl ether (3×30 cc). After drying, 5-(3-methoxyphenyl)amino-1,2-dithiol-3-thione (4.1 g), melting at 131°–134° C., is thus obtained.

Ethyl 3-(3-methoxyphenyl)amino-3-oxopropionate can be prepared by reacting m-anisidine (61.5 g) with ethyl chloroformylacetate (75.3 g), in the presence of triethylamine (50.5 g), in methylene chloride (500 cc) at a temperature of about 15° C. for 16 hours. After hydrolysis with distilled water (200 cc), the organic phase is washed successively with distilled water (200 cc), a 1 N aqueous solution of hydrochloric acid (200 cc) and distilled water (2×200 cc), dried over magnesium sulphate in the presence of decolorising charcoal, and filtered, and the filtrate is concentrated to dryness under reduced pressure (20 mm Hg; 2.7 kPa) at 60° C. This gives ethyl 3-(3-methoxyphenyl)amino-3-oxopropionate (108.6 g) in form of an orange-brown oil.

[Rf=0.2; chromatography on a thin layer of silica gel; solvent:methylene chloride].

EXAMPLE 49

A solution of dimethylcarbamoyl chloride (4.4 g) in acetone (20 cc) is added, in the course of 5 minutes, to a suspension of 5-(4-isopropylphenyl)amino-1,2-dithiol-3-thione (10 g) and sodium iodide (6.7 g) in acetone (130 cc) under reflux, and reflux is maintained for 18 hours. After cooling to a temperature of about 20° C., the insoluble product is filtered off and washed successively with acetone (2×20 cc), with distilled water (3×20 cc) and then with acetone (2×20 cc). This gives 5-dimethylcarbamoylthio-3-(4-isopropylphenyl)-imino-1,2-dithiole hydroiodide (4.85 g) melting at 160° C.

The corresponding base can be prepared in the following manner:

The salt obtained as described above is suspended in distilled water (45 cc). Sodium bicarbonate (1.1 g) and methylene chloride (70 cc) are then added with stirring. After stirring for 10 minutes, the organic phase is decanted, washed with distilled water (45 cc), dried over magnesium sulphate and filtered, and the filtrate is concentrated to dryness under reduced pressure (20 mm Hg; 2.7 kPa) at 40° C.

By recrystallisation of the resulting residue from hexane (350 cc), 5-dimethylcarbamoylthio-3-(4-isopropylphenyl)imino-1,2-dithiole (2.3 g), melting at 112° C., is obtained.

5-(4-Isopropylphenyl)amino-1,2-dithiol-3-thione can be prepared by reacting phosphorus pentasulphide (166.5 g) with ethyl 3-(4-isopropylphenyl)-amino-3-oxopropionate (124.7 g) in dioxan (1.25 liters) under reflux for 15 minutes. After cooling to a temperature of about 20° C., the reaction mixture is hydrolysed with a 20% aqueous solution of ammonia (d=0.92; 6 liters) for 45 minutes with stirring, and extracted with chloroform (1.5 liters) and then with chloroform (3×500 cc). The combined organic phases are washed with distilled water (500 cc), dried over magnesium sulphate and filtered, and the filtrate is concentrated to dryness under reduced pressure (20 mm Hg; 2.7 kPa) at 30° C. The residue obtained is triturated in methylene chloride (250 cc) and the insoluble product is filtered off and washed successively with methylene chloride (3×50 cc) and then with diisopropyl ether (2×100 cc). This gives 5-(4-isopropylphenyl)amino-1,2-dithiol-3-thione (38.1 g) melting at 213° C.

Ethyl 3-(4-isopropylphenyl)amino-3-oxopropionate can be prepared by reacting 4-isopropylaniline (109.4 g) with ethyl chloroformylacetate (113 g), in the presence of triethylamine (75.8 g), in methylene chloride (1 liters) at a temperature of about 20° C. for 16 hours. After hydrolysis with distilled water (500 cc), the organic phase is decanted and washed successively with distilled water (500 cc), a 1 N aqueous solution of hydrochloric acid (500 cc) and distilled water (4×500 cc), dried over magnesium sulphate in the presence of decolorising charcoal, and filtered, and the filtrate is concentrated to dryness under reduced pressure (20 mm Hg; 2.7 kPa) at 40° C. This gives ethyl 3-(4-isopropylphenyl)-amino-3-oxopropionate (190.4 g) in the form of an orange oil.

[Rf=0.6; chromatography on a thin layer of silica gel; solvent:methylene chloride and methanol (97.5/2.5 by volume)].

EXAMPLE 50

3-Methoxyphenacyl chloride (5.53 g) is added to a suspension of 5-morpholino-1,2-dithiol-3-thione (5.48 g) in ethanol (110 cc), and the reaction mixture is heated under reflux for 6 hours. After cooling to a temperature of about 20° C., the insoluble product is filtered off and washed with ethanol (2×20 cc). By recrystallisation of the resulting product from an ethanol/water mixture (4.4/1 by volume; 135 cc), N-[5-(3-methoxyphenacylthio)-1,2-dithiol-3-ylidene]-morpholinium chloride (5.7 g), melting at 140° C. with decomposition, is obtained.

EXAMPLE 51

2-Methoxyphenacyl bromide (5.15 g) is added to a suspension of 5-(pyrrolidin-1-yl)-1,2-dithiol-3-thione (3.05 g) and sodium iodide (3.7 g) in acetone (53 cc), and the reaction mixture is kept under reflux for 1 hour. After cooling, the insoluble product is filtered off and washed successively with acetone (3×20 cc), with water (3×20 cc) and then with diethyl ether (3×20 cc). After recrystallisation of the resulting product from ethanol (1000 cc), N-[5-(2-methoxyphenacylthio)-1,2-dithiol-3-ylidene]-pyrrolidinium iodide (5.3 g) melting at 205° C., is obtained.

EXAMPLE 52

3,4-Dihydroxyphenacyl chloride (7 g) is added to a suspension of 5-(pyrrolidin-1-yl)-1,2-dithiol-3-thione (5.1 g) and sodium iodide (6.2 g) in acetone (90 cc), and the reaction mixture is kept under reflux for 1 hour. After cooling, the insoluble product is filtered off and washed successively with acetone (3×20 cc), with water (3×20 cc) and then with diethyl ether (3×20 cc). By recrystallisation of the resulting product from a dimethylformamide/methanol mixture (20/80 by volume; 600 cc) and then desolvation by stirring for 30 minutes in water (100 cc), N-[5-(3,4-dihydroxyphenacylthio)-1,2-dithiol-3-ylidene]-pyrrolidinium iodide hydrate (6.9 g), melting at about 130° C., is obtained.

EXAMPLE 53

4-Fluorophenacyl chloride (2.6 g) is added to a solution of 5-(pyrrolidin-1-yl)-1,2-dithiol-3-thione (2.03 g) and sodium iodide (2.45 g) in acetone (35 cc), and the reaction mixture is kept under reflux for 2 hours. After cooling, the insoluble product is filtered off and washed successively with acetone (3×5 cc), with water (3×5 cc) and then with diethyl ether (3×5 cc). By recrystallisation of the resulting product from methanol (235 cc), N-[5-(4-fluorophenacylthio)-1,2-dithiol-3-ylidene]-pyrrolidinium iodide (2.75 g), melting at 192° C., is obtained.

EXAMPLE 54

A suspension of 5-morpholino-1,2-dithiol-3-thione (8 g) and 4-fluorophenacyl chloride (7.54 g) in ethanol (160 cc) is heated under reflux for 6 hours 30 minutes. After cooling to a temperature of about 20° C., the insoluble product formed is filtered off and washed successively with ethanol (3×30 cc) and diethyl ether (50 cc).

By recrystallisation of the resulting product from ethanol (220 cc), N-[5-(4-fluorophenacylthio)-1,2-dithiol-3-ylidene]-morpholinium chloride (12.3 g), melting at about 190° C., is obtained.

EXAMPLE 55

A suspension of 5-morpholino-1,2-dithiol-3-thione (2.7 g) and 4-hydroxyphenacyl chloride (2.52 g) in ethanol (54 cc) is heated under reflux for 8 hours. After cooling to a temperature of about 20° C., the insoluble product is filtered off and washed with ethanol (2×10 cc).

By recrystallisation of the resulting product from ethanol (100 cc), N-[5-(4-hydroxyphenacylthio)-1,2-dithiol-3-ylidene]-morpholinium chloride (3.1 g), melting at about 180° C., is obtained.

EXAMPLE 56

A suspension of 5-morpholino-1,2-dithiol-3-thione (8 g) and 4-chlorophenacyl chloride (9.2 g) in ethanol (160 cc) is heated under reflux for 10 hours. After cooling to a temperature of about 20° C., the insoluble product is filtered off and washed successively with ethanol (3×30 cc) and diethyl ether (50 cc).

By recrystallisation of the resulting product from a mixture of ethanol (450 cc) and water (50 cc), N-[5-(4-chlorophenacylthio)-1,2-dithiol-3-ylidene]-morpholinium chloride (8.85 g), melting at 160° C., is obtained.

EXAMPLE 57

2,4-Dichlorophenacyl chloride (9.8 g) is added all at once to a suspension of 5-morpholino-1,2-dithiol-3-thione (8 g) in ethanol (160 cc), and the suspension thus obtained is heated under reflux for 11 hours. After cooling to a temperature of about 20° C., the insoluble product is filtered off and washed successively with ethanol (3×30 cc) and diethyl ether (50 cc).

The product thus obtained is suspended in methylene chloride (150 cc) and, after stirring for 1 hour 30 minutes, the insoluble material is filtered off. After drying, N-[5-(2,4-dichlorophenacylthio)-1,2-dithiol-3-ylidene]-morpholinium chloride (8.2 g), melting at 260°–262° C., is obtained.

EXAMPLE 58

A suspension of 5-morpholine-1,2-dithiol-3-thione (8 g) and 4-ainophenacyl chloride (7.41 g) in ethanol (160 cc) is heated under reflux for 7 hours. After cooling to a temperature of about 20° C., the insoluble product is filtered off and washed with ethanol (2×20 cc).

The product thus obtained is deposited on silica gel (1 kg) contained in a column of diameter 4.5 cm. Elution is carried out successively with a methylene chloride/methanol mixture (99/1 by volume; 1000 cc), a methylene chloride/methanol mixture (98/2 by volume; 500 cc), a methylene chloride/methanol mixture (95/5 by volume; 500 cc) and a methylene chloride/methanol mixture (90/10 by volume; 1000 cc); the corresponding eluates are discarded. Elution is then carried out successively with a methylene chloride/methanol mixture (80/20 by volume; 1000 cc), a methylene chloride/methanol mixture (60/40 by volume; 1000 cc), a methylene chloride/methanol mixture (50/50 by volume; 1000 cc) and a methylene chloride/methanol mixture (25/75 by volume; 10000 cc); the corresponding eluates are combined and concentrated to dryness under reduced pressure (20 mm Hg; 2.7 kPa) at 40° C. The product thus obtained is suspended in methylene chloride (100 cc) and, after stirring for 15 minutes, the insoluble material is filtered off. After drying, N-[5-(4-aminophenacylthio)-1,2-dithiol-3-ylidene]-morpholinium chloride (7 g), melting at 220° C., is obtained.

EXAMPLE 59

A suspension of 5-morpholino-1,2-dithiol-3-thione (8 g) and 4-cyanophenacyl chloride (8.7 g) in ethanol (160 cc) is heated under reflux for 6 hours. After cooling to a temperature of about 20° C., the insoluble product is filtered off and washed successively with ethanol (3×30 cc), carbon disulphide (30 cc) and diethyl ether (30 cc).

By recrystallisation of the resulting product from a mixture of ethanol (900 cc) and water (100 cc), N-[5-(4-cyanophenacylthio)-1,2-dithiol-3-ylidene]-morpholinium chloride (9.8 g), melting at 198° C., is obtained.

EXAMPLE 60

A suspension of 5-morpholino-1,2-dithiol-3-thione (8 g) and 3-chlorophenacyl chloride (8.8 g) in ethanol (160 cc) is heated under reflux for 6 hours. After cooling to a temperature of about 20° C., the insoluble product is filtered off and washed successively with ethanol (3×30 cc) and diethyl ether (50 cc).

By recrystallisation of the resulting product from a mixture of ethanol (315 cc) and water (35 cc), a product (10.4 g) is obtained melting at 180° C. This product is washed with carbon disulphide (2×40 cc). By recrystallisation from a mixture of ethanol (315 cc) and water (35 cc), N-[5-(3-chlorophenacylthio)-1,2-dithiol-3-ylidene]-morpholinium chloride (8.05 g), melting at about 175° C., is obtained.

EXAMPLE 61

A suspension of 5-morpholino-1,2-dithiol-3-thione (5 g), 2-chlorophenacyl chloride (7.6 g) and sodium iodide (5.6 g) in acetone (115 cc) is heated under reflux for 30 minutes. After cooling to a temperature of about 20° C., the insoluble product is filtered off and washed successively with acetone (20 cc), water (20 cc) and diethyl ether (20 cc).

By recrystallisation of the resulting product from a mixture of ethanol (175 cc) and water (175 cc), N-[5-(2-chlorophenacylthio)-1,2-dithiol-3-ylidene]-morpholinium iodide (6.75 g), melting at 156° C., is obtained.

EXAMPLE 62

A suspension of 5-morpholino-1,2-dithiol-3-thione (7.9 g) and 4-methylphenacyl chloride (13.55 g) in ethanol (160 cc) is heated under reflux for 67 hours. The insoluble product is filtered off at a temperature of about 60° C. and the filtrate is evaporated to dryness under reduced pressure (20 mm Hg; 2.7 kPa). The residue thus obtained is dissolved in methylene chloride (100 cc) and the product which crystallises is filtered off and then resuspended in methylene chloride (100 cc). After stirring for 30 minutes at a temperature of about 20° C. the insoluble material is filtered off. This gives N-[5-(4-methylphenacylthio)-1,2-dithiol-3-ylidene]-morpholinium chloride (4.6 g) melting at 160°–164° C.

EXAMPLE 63

Methyl iodide (3.4 g) is added to a solution of 5-dimethylcarbamoylthio-3-phenylimino-1,2-dithiole (2.37 g), prepared as described in Example 32, in acetone (50 cc) under reflux, and reflux is maintained for 3 hours. After cooling to a temperature of about 20° C., the insoluble product formed is filtered and washed with acetone (10 cc).

After recrystallisation from acetonitrile (100 cc), N-methyl-N-(5-dimethylcarbamoylthio-1,2-dithiol-3-ylidene)-phenylammonium iodide (2.1 g), melting at 230° C., is obtained.

EXAMPLE 64

A suspension of 5-morpholino-1,2-dithiol-3-thione (2.62 g), 4-methoxyphenacyl bromide (4.12 g) and sodium iodide (3 g) in acetone (60 cc) is heated to the reflux temperature and maintained there for 2 hours. After cooling to a temperature of about 20° C., the insoluble product is filtered off and washed successively with acetone (30 cc), distilled water (2×40 cc) and acetone (2×30 cc). The product thus obtained is suspended in methylene chloride (110 cc). After stirring for 1 hour at a temperature of about 20° C., the insoluble product is separated by filtration. N-[5-(4-Methoxyphenacylthio)-1,2-dithiol-3-ylidene]-morpholinium iodide, melting at 152°-155° C., is thus obtained.

The present invention also relates to the pharmaceutical compositions which comprise a compound of general formula (I) in the form of a pharmaceutically acceptable salt or, if appropriate, in the free base form, in accordance with any other pharmaceutically compatible product, which can be inert or physiologically active. The compositions according to the invention can be administered orally, parenterally or rectally.

Tablets, pills, powders (in particular in gelatin capsules or cachets) or granules, can be used as solid compositions for oral administration. In these compositions, the active product according to the invention is mixed with one or more inert diluents, such as starch, cellulose, sucrose, lactose or silica. These compositions can also comprise substances other than diluents, e.g. one or more lubricants, such as magnesium stearate or talc, a colorant, a coating (coated tablets) or a lacquer.

Liquid compositions for oral administration include pharmaceutically-acceptable solutions, suspensions, emulsions, syrups and elixirs containing inert diluents, such as water, ethanol, glycerol, vegetable oils or paraffin oil. Besides inert diluents such compositions may also comprise adjuvants such as wetting, sweetening, thickening, flavouring or stabilising agents.

Preparations according to the invention for parenteral administration include sterile aqueous or nonaqueous solutions, suspensions or emulsions. Water, propylene glycol, a polyethylene glycol, vegetable oils, in particular olive oil, injectable organic esters, e.g. ethyl oleate, or other suitable organic solvents can be employed as the solvent or vehicle. These compositions may also contain adjuvants, in particular wetting agents, isotonic agents, emulsifiers, dispersing agents and stabilisers. Sterilisation can be carried out in several ways, e.g., by filtration under aseptic conditions, by incorporating sterilising agents into the composition, by irradiation or by heating. The compositions can also be prepared in the form of sterile solid compositions which can be dissolved in an injectable sterile medium immediately before use.

Compositions for rectal administration are suppositories or rectal capsules, which, in addition to the active product, contain excipients, such as cacao butter, semisynthetic glycerides or polyethylene glycols.

In human therapy, the compounds according to the invention are particularly useful as cytoprotective agents in the treatment of ulcers of the digestive system. The doses depend on the desired effect and on the duration of the treatment; adult doses are generally between 7 and 700 mg per day, administered orally in one or more portions.

In general, the physician will determine the dosage considered most appropriate, taking into account the age, the weight and all of the other factors intrinsic to the patient being treated.

The following Examples illustrate pharmaceutical compositions according to the invention.

EXAMPLE 65

Tablets containing 50 mg doses of active product and having the following composition are prepared in accordance with the usual technique:

| | |
|---|---|
| N—[5-(3-methoxyphenacylthio)-1,2-dithiol-3-ylidene]-morpholinium chloride | 50 mg |
| starch | 60 mg |
| lactose | 50 mg |
| magnesium stearate | 2 mg |

EXAMPLE 66

Tablets containing 50 mg doses of active product and having the following composition are prepared in accordance with the usual technique:

| | |
|---|---|
| N—[5-(4-fluorophenacylthio)-1,2-dithiol-3-ylidene]-pyrrolidinium iodide | 50 mg |
| starch | 60 mg |
| lactose | 50 mg |
| magnesium stearate | 2 mg |

We claim:

1. A 1,2-dithiol-3-ylideneammonium derivative of the general formula:

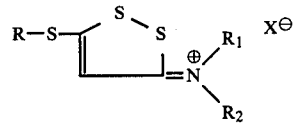

wherein $X^\ominus$ represents an pharmaceutically acceptable anion, R represents a straight- or branched-chain alkyl radical containing 1 to 7 carbon atoms [unsubstituted or substituted by a hydroxy, carboxy, alkoxycarbonyl, cyano, dialkylamino or alkylcarbonyl radical, or a benzoyl radical the phenyl ring of which is unsubstituted or substituted by one or more halogen atoms or radicals selected from alkyl (optionally substituted by one or more halogen atoms), alkoxy, hydroxy, amino, alkylamino, dialkylamino, cyano and nitro, or by a thenoyl radical the thienyl ring of which is unsubstituted or substituted by one or more halogen atoms or radicals selected from alkyl, cyano and nitro, or a pyridylcarbonyl, carbamoyl, dialkylcarbamoyl (the alkyl radicals of which can together form, with the nitrogen atom to which they are attached, a 5- or 6-membered heterocyclic ring optionally containing another heteroatom selected from oxygen, sulphur, and nitrogen substituted by an alkyl or alkylcarbonyl radical) or pyridyl radical], a dialkylcarbamoyl radical (the alkyl radicals of which can together form, with the nitrogen atom to which they are attached, a 5- or 6-membered heterocyclic ring optionally containing another heteroatom selected from oxygen, sulphur, and nitrogen substituted by an alkyl or alkycarbonyl radical), an alkenyl radical containing 2 to 4 carbon atoms, an alkynyl radical containing 2 to 4 carbon atoms, or an alkoxycarbonyl radical, or alternatively represents a 2-oxotetrahydrofuran-3-yl or 2-oxotetrahydropyran-3-yl ring, and either $R_1$ and $R_2$, which have the same or different significances, each represent a phenyl radical, a cycloalkyl radical containing 3 to 7 carbon atoms, or an alkyl or phenylalkyl radical, or alternatively together form, with the nitrogen atom to which they are attached, a 5-, 6- or 7-membered heterocyclic ring which can optionally contain another hetero-atom selected from oxygen, sulphur, and nitrogen substituted by an alkyl radical, or $R_1$ represents a phenyl radical unsubstituted or substituted by one or more halogen atoms or radicals selected from alkyl (optionally substituted by one or more halogen atoms), alkoxy, hydroxy, amino, alkylamino, dialkylamino, cyano and nitro, or alternatively represents a cycloalkyl radical containing 3 to 7 carbon atoms, or an alkyl or phenylalkyl radical, and $R_2$ represents a hydrogen atom, and also the corresponding bases when $R_2$ represents a hydrogen atom, the aforementioned alkyl and alkoxy radicals and moieties containing 1 to 4 carbon atoms in a straight- or branched-chain unless otherwise indicated.

2. A compound according to claim 1 wherein $X^\ominus$ represents an pharmaceutically acceptable anion, R represents a straight- or branched-chain alkyl radical containing 1 to 7 carbon atoms [unsubstituted or substituted by a hydroxy, carboxy, alkoxycarbonyl, cyano, dialkylamino, alkylcarbonyl, benzoyl, thenoyl, pyridylcarbonyl, carbamoyl, dialkylcarbamoyl (the alkyl radicals of which can together form, with the nitrogen atom to which they are attached, a 5- or 6-membered heterocyclic ring optionally containing another hetero-atom selected from oxygen, sulphur, and nitrogen substituted by an alkyl or alkylcarbonyl radical) or pyridyl radical], a dialkylcarbamoyl radical (the alkyl radicals of which can together form, with the nitrogen atom to which they are attached, a 5- or 6-membered heterocyclic ring optionally containing another hetero-atom selected from oxygen, sulphur, and nitrogen substituted by an alkyl or alkylcarbonyl radical), an alkenyl radical containing 2 to 4 carbon atoms or an alkynyl radical containing 2 to 4 carbon atoms, and either $R_1$ and $R_2$, which have the same or different significances, each represent a phenyl radical, a cycloalkyl radical containing 3 to 7 carbon atoms, or an alkyl or phenylalkyl radical, or alternatively together form, with the nitrogen atom to which they are attached, a 5-, 6- or 7-membered heterocyclic ring which can optionally contain another hetero-atom selected from oxygen, sulphur, and nitrogen substituted by an alkyl radical, or $R_1$ represents a phenyl radical, a cycloalkyl radical containing 3 to 7 carbon atoms, or an alkyl or phenylalkyl radical, and $R_2$ represents a hydrogen atom, and also the corresponding bases when $R_2$ represents hydrogen, the aforementioned alkyl and alkoxy radicals and moieties containing 1 to 4 carbon atoms in a straight- or branched-chain unless otherwise mentioned.

3. A compound according to claim 1 wherein $X^\ominus$ represents an pharmaceutically acceptable anion, R represents an alkenyl radical containing 2 to 4 carbon atoms, or a straight- or branched-chain alkyl radical containing 1 to 7 carbon atoms [unsubstituted or substituted by a cyano, dialkylamino, carbamoyl, alkylcarbonyl or thenoyl radical, or a benzoyl radical the phenyl ring of which is unsubstituted or substituted by one or more halogen atoms or radicals selected from alkyl, alkoxy, hydroxy and cyano], the aforementioned alkyl and alkoxy radicals and moieties containing 1 to 4 carbon atoms in a straight- or branched-chain unless otherwise stated, and $R_1$ and $R_2$ together with the nitrogen atom to which they are attached represent a pyrrolidin-1-yl or morpholino radical.

4. A compound according to claim 1 wherein $X^\ominus$ represents an pharmaceutically acceptable anion, R represents a methyl or ethyl radical unsubstituted or substituted by a benzoyl radical the phenyl ring of which is unsubstituted or substituted by one or more halogen atoms or radicals selected from alkyl and alkoxy radicals containing 1 to 4 carbon atoms in a straight- or branched-chain, and the hydroxy and cyano radicals, and $R_1$ and $R_2$ together with the nitrogen atom to which they are attached represent the morpholino radical.

5. A 1,2-dithiol-3-ylideneammonium derivative according to claim 1 which is N-[5-(4-chlorophenacylthio)-1,2-dithiol-3-ylidene]-morpholinium chloride.

6. A 1,2-dithiol-3-ylideneammonium derivative according to claim 1 which is N-[5-(3-methoxyphenacylthio)-1,2-dithiol-3-ylidene]-morpholinium chloride.

7. A 1,2-dithiol-3-ylideneammonium derivative according to claim 1 which is N-[5-(4-fluorophenacylthio)-1,2-dithiol-3-ylidene]-morpholinium chloride.

8. A 1,2-dithiol-3-ylideneammonium derivative according to claim 1 which is N-[5-(2,4-dichlorophenacylthio)-1,2-dithiol-3-ylidene]-morpholinium chloride.

9. A 1,2-dithiol-3-ylideneammonium derivative according to claim 1 which is N-[5-(2-chlorophenacylthio)-1,2-dithiol-3-ylidene]-morpholinium iodide.

10. A 1,2-dithiol-3-ylideneammonium derivative according to claim 1 which is N-[5-(4-hydroxyphenacylthio)-1,2-dithiol-3-ylidene]-morpholinium chloride.

11. A 1,2-dithiol-3-ylideneammonium derivative according to claim 1 which is N-[5-(4-methoxyphenacylthio)-1,2-dithiol-3-ylidene]-morpholinium iodide.

12. A 1,2-dithiol-3-ylideneammonium derivative according to claim 1 which is N-[5-(4-methylphenacylthio)-1,2-dithiol-3-ylidene]-morpholinium chloride.

13. A 1,2-dithiol-3-ylideneammonium derivative according to claim 1 which is N-[5-(4-cyanophenacylthio)-1,2-dithiol-3-ylidene]-morpholinium chloride.

14. A 1,2-dithiol-3-ylideneammonium derivative according to claim 1 which is N-[5-(phenacylthio)-1,2-dithiol-3-ylidene]-morpholinium chloride.

15. Pharmaceutical compositions which comprise a pharmaceutically acceptable 1,2-dithiol-3-ylideneammonium derivative conforming to the general formula depicted in claim 1 or, when $R_2$ represents hydrogen, a base derived therefrom, in association with a pharmaceutically acceptable carrier.

16. A method for the treatment of a patient suffering from ulceration of the digestive system which comprises administering to the patient an amount of a pharmaceutically acceptable 1,2-dithiol-3-ylideneammonium derivative conforming to the general formula depicted in claim 1 or, when $R_2$ represents hydrogen, a base derived thereforom, effective to ameliorate the condition of the patient.

* * * * *